(12) United States Patent
Paudel et al.

(10) Patent No.: US 11,726,032 B2
(45) Date of Patent: Aug. 15, 2023

(54) SYSTEM AND METHOD OF DETERMINING ISSUES WITH OPTICAL COMPONENTS

(71) Applicant: ALCON INC., Fribourg (CH)

(72) Inventors: Arun Paudel, Berlin (DE); Olaf Kittelmann, Berlin (DE); Matthias Foesel, Memmelsdorf (DE)

(73) Assignee: Alcon Inc., Fribourg (CH)

( * ) Notice: Subject to any disclaimer, the term of this patent is extended or adjusted under 35 U.S.C. 154(b) by 186 days.

(21) Appl. No.: 17/119,827

(22) Filed: Dec. 11, 2020

(65) Prior Publication Data

US 2021/0181096 A1 Jun. 17, 2021

Related U.S. Application Data

(60) Provisional application No. 62/947,699, filed on Dec. 13, 2019.

(51) Int. Cl.
*G01N 21/31* (2006.01)
*G02B 21/00* (2006.01)
*G02B 26/10* (2006.01)

(52) U.S. Cl.
CPC ....... *G01N 21/3103* (2013.01); *G02B 21/002* (2013.01); *G02B 26/10* (2013.01)

(58) Field of Classification Search
CPC .. G01N 21/3103; G02B 21/002; G02B 26/10; A61F 9/008; G01M 11/0278
See application file for complete search history.

(56) References Cited

U.S. PATENT DOCUMENTS

| 3,892,494 | A | 7/1975 | Baker et al. |
| 6,466,040 | B1* | 10/2002 | Simon ................. G02B 21/002 |
| | | | 324/762.05 |
| 8,932,352 | B2* | 1/2015 | Knox ..................... C08J 7/123 |
| | | | 351/159.01 |
| 9,545,340 | B1* | 1/2017 | Knox ................. A61F 9/00827 |
| 10,962,752 | B2* | 3/2021 | Judkewitz ........... A61B 5/0059 |
| 11,148,225 | B2* | 10/2021 | Marjanovic ............ C03C 15/00 |
| 11,345,625 | B2* | 5/2022 | Grundmueller ....... C03B 33/091 |

(Continued)

FOREIGN PATENT DOCUMENTS

| CN | 105890875 A | * | 8/2016 | ............ G01M 11/02 |
| CN | 109443711 A | | 3/2019 | |

(Continued)

*Primary Examiner* — Mohamed K Amara

(57) ABSTRACT

The disclosure provides a system that may: provide multiple first portions of a laser beam to an objective lens of an optical system; provide the multiple first portions of the laser beam to respective multiple locations of a test surface; receive multiple second portions of the laser beam from the test surface; determine multiple intensities respectively associated with the multiple second portions of the laser beam; transform the multiple intensities into data that represents multiple measurement values of the multiple intensities; determine, from the data, if an intensity value of the multiple intensities is below a threshold intensity value; if the intensity is below the threshold intensity value, provide information that indicates an issue associated with the objective lens; and if the intensity is not below the threshold intensity value, provide information that indicates there is no issue associated with the objective lens.

24 Claims, 16 Drawing Sheets

(56) References Cited

U.S. PATENT DOCUMENTS

| | | | |
|---|---|---|---|
| 2009/0137990 A1* | 5/2009 | Sheinis | G02B 21/0072 606/5 |
| 2013/0056910 A1* | 3/2013 | Houbertz-Krauss | B29C 64/386 264/401 |
| 2015/0077844 A1* | 3/2015 | Singer | G02B 21/0032 359/385 |
| 2015/0133901 A1* | 5/2015 | Serdarevic | A61F 9/0079 606/5 |
| 2019/0204574 A1* | 7/2019 | Judkewitz | G02B 26/06 |
| 2020/0266601 A1 | 8/2020 | Goos et al. | |
| 2020/0377956 A1* | 12/2020 | Vogelstein | C12Q 1/686 |
| 2021/0177256 A1* | 6/2021 | Paudel | A61B 3/107 |
| 2021/0177658 A1* | 6/2021 | Paudel | A61B 3/1025 |
| 2022/0236547 A1* | 7/2022 | Qu | G02B 21/0048 |

FOREIGN PATENT DOCUMENTS

| | | | | |
|---|---|---|---|---|
| CN | 109974977 A | | 7/2019 | |
| CN | 109974977 B | * | 1/2021 | ........ G01M 11/0242 |

\* cited by examiner

SYSTEM AND METHOD OF DETERMINING ISSUES WITH OPTICAL COMPONENTS

BACKGROUND

Field of the Disclosure

This disclosure relates to determining if an optical unit should be replaced or repaired and more particularly to utilizing intensities of reflected light from a test surface to determine if an optical unit should be replaced or repaired.

Description of the Related Art

In the past, it was not been possible to determine the quality of complex optical units, such as F-theta lenses, without special and expensive measuring instruments. These special measuring instruments were usually available from producers of the complex optical units. An example of a special measuring instrument that can determine the quality of complex optical units is a wavefront sensor. For example, the wavefront sensor may be specifically designed for the parameters of a complex optical unit. The special measuring instrument may provide detailed information that may not be necessary to determine if a complex optical unit should be replaced during final device assembling or field service action. Without needing such unnecessary information, other one or more systems, one or more processes, and/or one or more methods may be implemented to determine if a complex optical unit should be replaced.

SUMMARY

The present disclosure provides a system that may provide multiple first portions of a laser beam to an objective lens of an optical system; may provide the multiple first portions of the laser beam to respective multiple locations of a test surface; may receive multiple second portions of the laser beam from the test surface; provide the multiple second portions of the laser beam to a two-photon absorption (TPA) detector; may determine multiple intensities respectively associated with the multiple second portions of the laser beam; may transform the multiple intensities into data that represents multiple measurement values of the multiple intensities; may determine, from the data, if an intensity value of the multiple intensities is below a threshold intensity value; if the intensity value of the multiple intensities is not below the threshold intensity value, may provide information that indicates there is no issue associated with the objective lens; and if the intensity value of the multiple intensities is below the threshold intensity value, may provide information that indicates an issue associated with the objective lens. For example, the issue associated with the objective lens may be an optical aberration.

The system may include a laser that generates the laser beam. The system may include a biometry device that may include the optical system. The optical system may include at least one mirror. For example, the system may further adjust the at least one mirror to provide the multiple first portions of the laser beam to the respective multiple locations of the test surface. The system may include multiple lenses, different from the objective lens. For example, the system may further adjust the multiple lenses to expand respective diameters of the multiple first portions of the laser beam. The system may include a diaphragm. For example, the system may further adjust a diameter of an aperture of the diaphragm. The diaphragm may permit light, reflected from the test surface, to pass through the aperture and may block the light, reflected from the test surface, outside the aperture. For example, the test surface may be partially reflective.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) provide multiple first portions of a laser beam to the objective lens of the optical system; ii) provide, via the objective lens, the multiple first portions of the laser beam to respective multiple locations of a test surface; iii) receive, via the objective lens, multiple second portions of the laser beam from the test surface; iv) provide the multiple second portions of the laser beam to the TPA detector; v) determine multiple intensities respectively associated with the multiple second portions of the laser beam; vi) transform the multiple intensities into data that represents multiple of measurement values of the multiple intensities; vii) determine, from the data, if an intensity value of the multiple intensities is below a threshold intensity value; viii) if the intensity value of the multiple intensities is below the threshold intensity value, provide information that indicates an issue associated with the objective lens; ix) if the intensity value of the multiple intensities is not below the threshold intensity value, provide information that indicates there is no issue associated with the objective lens; x) generate the laser beam; xi) adjust the at least one mirror to provide the multiple first portions of the laser beam to the respective multiple locations of the test surface; and xii) adjust a diameter of an aperture of a diaphragm.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1A:
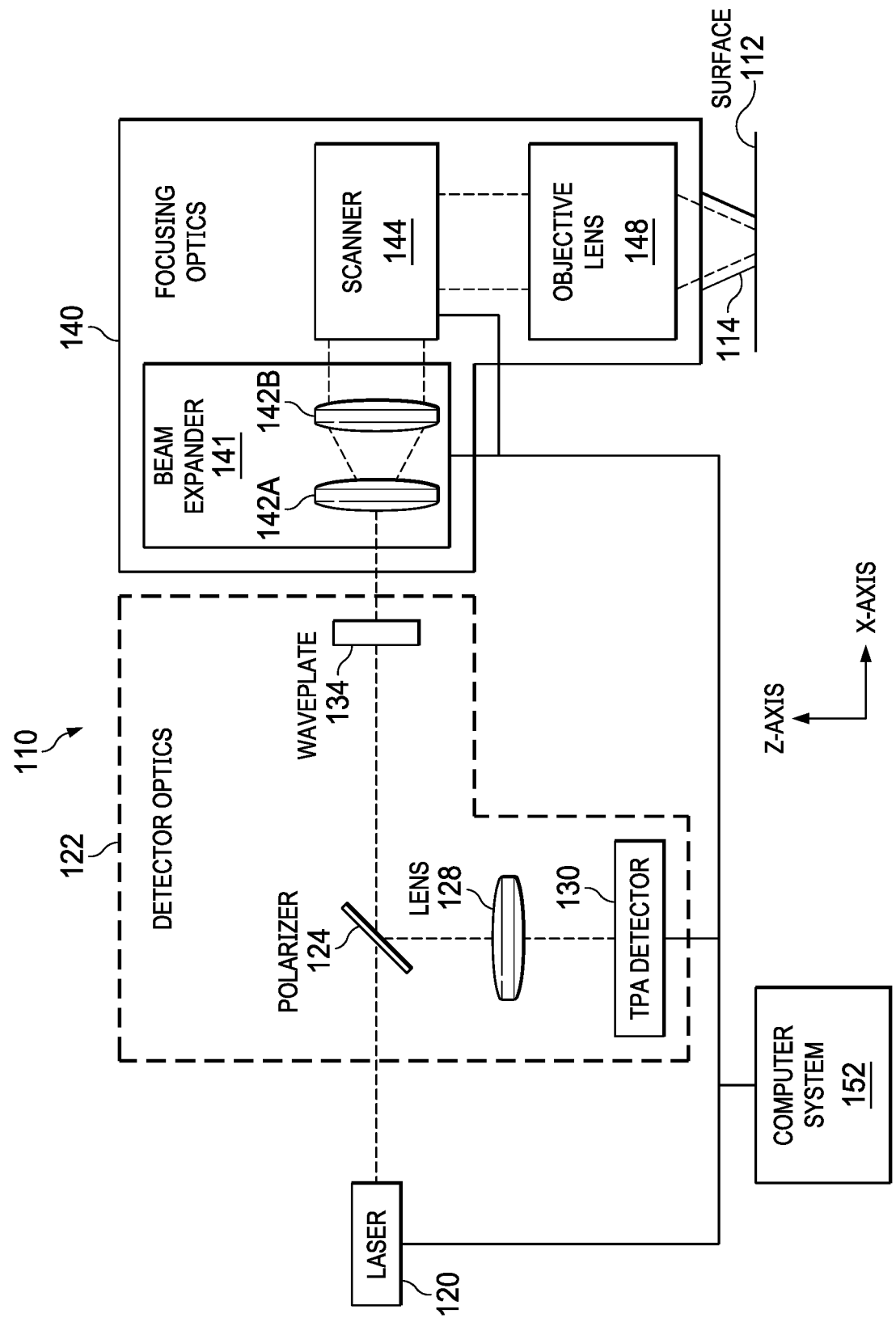
FIG. 1A illustrates an example of an optical system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

Medical systems may be utilized in performing medical procedures with patients. Medical systems may include optics. For example, a medical system may include one or more optical systems that may include optics. An optical system may include one or more optical devices. For example, an optical device may be or may include a device that controls light (e.g., reflects light, refracts light, filters light, transmits light, polarizes light, etc.). An optical device may be made of any material that controls the light as designed. For example, the material may include one or more of glass, crystal, metal, and semiconductor, among others. Examples of optical devices may include one or more of lenses, mirrors, prisms, optical filters, waveguides, waveplates, beam expanders, beam collimators, beam splitters, gratings, and polarizers, among others. While an optical system may be designed for consistency, the optical system may be tested. For example, the optical system may be periodically tested to determine if the optical system is functioning according to one or more parameters.

An optical system may be tested utilizing a surface. For example, the surface may include only a few aberrations. The surface may be configured to emulate an ideal surface. In one example, the aberrations of the surface may not produce false-positives when utilized in testing an optical system. In another example, the aberrations of the surface may produce a number of false-positives, when utilized in testing an optical system, that are within a tolerance.

An optical system may include a two-photon absorption detector. For example, one or more processes and/or one or more methods utilized in testing the optical system may take advantage of one or more effects of two-photon absorption. During testing, an offset value may be set during focus control to characterize a quality of the optical system by way of deviations from an expected location of an offset depth in reflections from a surface. The reflections may be analyzed to determine if the optical system has any locally definable deficiencies.

One or more characterization of complex optical devices, such as a F-theta objective lens, may be possible utilizing one or more systems, one or more processes, and/or one or more methods described herein. For example, one or more characterization of complex optical devices, such as a F-theta objective lens, may be possible without utilizing special and/or expensive measuring instruments such as wavefront sensors, which may be specifically designed for specific parameters of the optical devices.

Turning now to FIG. 1A, an example of an optical system is illustrated. An optical system 110 may calibrate a position of a focal point of a laser beam directed to a target. For example, the target may be a surface 112. Surface 112 may be referred to as a reference surface. Surface 112 may be referred to as a test surface. Surface 112 may be utilized in determining if one or more portions of optical system 110 may be utilized in one or more procedures. Surface 112 may be utilized in determining if one or more portions of optical system 110 may be utilized in one or more medical procedures. For example, if the one or more portions of optical system 110 may not be utilized in the one or more medical procedures, the one or more portions of optical system 110 may be repaired or may be replaced. Surface 112 may be a surface of a test material that mimics a portion of a patient. Surface 112 may be a surface of a test material to calibrate optical system 110. Surface 112 may be a surface of a test material that mimics a portion of a patient. In one example, surface 112 may be completely reflective. In another example, surface 112 may be partially reflective. As an example, the test material may include polymethyl methacrylate (PMMA). PMMA may mimic an eye of a patient. For example, PMMA may mimic one or more reflections of light off an eye of a patient.

Optical system 110 may be utilized in a medical procedure. For example, the medical system may include optical system 110. The medical procedure may include an ophthalmic procedure on at least a portion part of an eye of a patient. Although optical system 110 may be utilized in a medical system, optical system 110 may be utilized in any system. As an example, optical system 110 may be utilized with a telescope. The telescope may be a reflecting telescope.

Optical system 110 may include multiple optical devices. For example, an optical device may be or may include a device that controls light (e.g., reflects light, refracts light, filters light, transmits light, polarizes light, etc.). An optical device may be made of any material that controls the light as designed. For example, the material may include one or more of glass, crystal, metal, and semiconductor, among others. Examples of optical devices may include one or more of lenses, mirrors, prisms, optical filters, waveguides, waveplates, beam expanders, beam collimators, beam splitters, gratings, and polarizers, among others.

As shown, optical system 110 may include a laser 120. Laser 120 may generate a laser beam. In one example, the laser beam may be a pulsed laser beam. In another example, the laser beam may be a continuous wave laser beam. Laser 120 may be a device that generates a beam of coherent monochromatic light by stimulated emission of photons from excited atoms or molecules. A laser beam may have any suitable wavelength, e.g., a wavelength in the infrared (IR), in the visible, or ultraviolet (UV) range, among others. Pulses of the laser beam may have a pulse duration in any suitable range, e.g., the microsecond, nanosecond, picosecond, femtosecond, or attosecond range, among others. The focus of the laser beam may be a focal point of the laser beam. As illustrated, optical system may include detector optics 122 and focusing optics 140. As shown, detector optics 122 may include a polarizer 124, a lens 128, a two-photon absorption (TPA) detector 130, and a waveplate 134. Although lens 128 is shown as a single lens, lens 128 may be multiple lenses.

Polarizer 124 may be an optical filter that transmits light of a specific polarization direction while reflecting light of other polarization directions. Polarizer 124 may filter light of undefined or mixed polarization into light with a single linear polarization. In one example, polarizer 124 may transmit at least a portion of the laser beam received from laser 120 (which may have a first polarization) towards waveplate 134. In another example, polarizer 124 may reflect at least portion of the laser beam received from waveplate 134 (which may have a second polarization) towards lens 128 and TPA detector 130. The first polarization may be a linear polarization. The second polarization may be the linear polarization rotated by ninety degrees (90°). Lens 128 may focus the beam from polarizer 124 to TPA detector 130. For example, TPA detector 130 may be located at a focal plane of lens 128. Lens 128 may be an achromatic lens. For example, lens 128 may be configured to limit effects of one or more chromatic aberrations and/or one or more spherical aberrations, among others.

Waveplate 134 may be an optical device that alters a polarization of light travelling through it. Waveplate 134 may be any suitable waveplate, e.g., a quarter-waveplate, which may convert linearly polarized light into circularly polarized light and vice versa, or a combination of a half-waveplate (which may rotate linearly polarized light by forty-five degrees (45°)) and a forty-five degree (45°) Faraday rotator (also known as an optical diode when used in combination with polarizer 124). Waveplate 134 may be a quarter-waveplate that may receive the laser beam with a first linear polarization from polarizer 124. Waveplate 134 may convert the laser beam from the first linear polarization to a circular polarization. Waveplate 134 may direct the laser beam to focusing optics 140. Waveplate 134 may receive at least a reflected portion of the laser beam from focusing optics 140. Waveplate 134 may convert the at least the reflected portion of the laser beam from focusing optics 140 from a circular polarization to a second linear polarization rotated relative to a first linear polarization. Waveplate 134 may change the original linear polarization of the laser beam by ninety degrees (90°).

Waveplate 134 may include a combination of a half-waveplate and a Faraday rotator. Waveplate 134 may receive the laser beam with a first linear polarization from polarizer 124. In this direction, the half-waveplate and the Faraday rotator may compensate for each other's rotational effect, which may result in a rotation of the laser beam by zero degrees (0°). Waveplate 134 may then direct the laser beam to focusing optics 140. Waveplate 134 may also receive the at least the reflected portion of the laser beam reflected from focusing optics 140. In this direction, the half-waveplate and the Faraday rotator may add rotational effects, which may result in a rotation of the laser beam by ninety degrees (90°), which may be a second linear polarization rotated relative to the first linear polarization. For example, the laser beam may pass through waveplate 134, which may rotate the beam by zero degrees (0°), and may be reflected back through waveplate 134, which may rotate the beam by ninety degrees (90°), resulting in a change from the original linear polarization of the laser beam by ninety degrees (90°). Waveplate 134 may be reconfigured such that the laser beam may pass through waveplate 134, which may rotate the beam by ninety degrees (90°), and may be reflected back through waveplate 134, which may rotate the beam by zero degrees (0°).

Although not specifically illustrated, optical system 110 may not include waveplate 134. For example, polarizer 124 may be replaced with a partially reflecting mirror. Although not specifically illustrated, detector optics 122 may be positioned between beam expander 141 and scanner 144.

As illustrated, focusing optics 140 may include a beam expander 141, a scanner 144, and an objective lens 148. Objective lens 148 may include multiple lenses. In one example, objective lens 148 may be or include a compound lens. In another example, objective lens 148 may be or include a F-theta lens. As shown, beam expander 141 may include lenses 142A and 142B. Although beam expander 141 is shown with two lenses, beam expander 141 may include any number of lenses.

A direction of the laser beam, as the laser beam approaches surface 112, may be parallel to a Z-axis. Surface 112 may be parallel to a X-axis and perpendicular to the Z-axis. Although a Y-axis is not specifically illustrated, the Y-axis may be perpendicular to the X-axis and the Z-axis. For example, the Y-axis may be perpendicular to a plane that includes the X-axis and the Z-axis. A direction of the laser beam, as the laser beam approaches surface 112, may not be parallel to the Z-axis. For example, an issue associated with objective lens 148 may cause the direction of the laser beam, as the laser beam approaches surface 112, to not be parallel to the Z-axis.

Focusing optics 140 may direct and/or may focus the laser beam towards surface 112. Focusing optics 140 may direct a focal point of the laser beam along the Z-axis towards surface 112 and may receive at least a portion of the beam reflected by surface 112. An optical device, such as a lens 142A and/or a mirror, may control a Z-position of a focal point of a laser beam. Another optical device, such as a lens 142B (e.g., in combination with lens 142A), may expand a diameter of a laser beam. In one example, beam expander 141 may be configured to consistently control a focal point of a laser beam. In another example, optics may vary over time such that the Z-position of the focal point changes. One or more calibrations of the Z-position of the focal point of the laser beam may be measured from time to time.

Scanner 144 may include one or more optical devices that may control a direction of a laser beam to control the XY-position of the focal point. To transversely deflect the laser beam, scanner 144 may include a pair of galvanometric actuated scanner mirrors that may tilt about mutually perpendicular axes. Scanner 144 may receive the laser beam from beam expander 141. Scanner 144 may manipulate the laser beam to control the XY-position of the focal point. Objective lens 148 may receive the laser beam from the scanner 144. Objective lens 148 may direct the beam to surface 112.

An interface 114 may stabilize a position of surface 112 relative to optical system 110. For example, interface 114 may be made of one or more rigid materials (e.g., plastic, glass, metal, etc.). Interface 114 may be a patient interface 114. For example, a patient interface 114 may shape an eye (e.g., flatten or otherwise deform) a surface of the eye. A "target-side" surface of patient interface 114 may be the surface of interface 114 designed to face (and may even be in contact with) an eye. A patient interface 114 may be a one-time-use product. For example, a patient interface 114 may be utilized with an eye of a patient and then discarded. Multiple patient interfaces 114 may be configured with a consistent length in a Z-direction. Multiple patient interfaces 114 may have different respective lengths. A calibration of a Z-position of a point with respect to a particular interface 114 may be performed.

As illustrated, optical system 110 may include a computer system 152. Computer system 152 may execute instructions in implementing at least a portion of one or more systems, one or more flow charts, one or more processes, and/or one or more methods described herein. Although optical system 110 is illustrated as including computer system 152, optical system 110 may not include computer system 152. For example, computer system 152 may be external to optical system 110. Computer system 152 may be communicatively coupled to optical system 110.

Focusing optics 140 may direct a laser beam to surface 112. For example, surface 112 may be located at an end of an interface 114. Surface 112 may reflect the laser beam. Surface 112 may reflect at least a portion of the laser beam. Detector optics 122 may direct the at least the portion of the laser beam to TPA detector 130. For example, TPA detector 130 may transform an intensity of the at least the portion of the laser beam into digital data. The digital data may represent the intensity of the at least the portion of the laser beam. TPA detector 130 may provide the digital data to computer system 152.

The at least the portion of the laser beam may cause two-photon absorption that may excite electrons, which may generate a signal in response to an intensity of incident radiation. The signal may indicate a proximity of a focal point of the laser beam to surface 112. In one example, the farther away the focal point is from surface 112, the lower an intensity of the beam at a portion TPA detector 130. In a second example, the larger a diameter of the at least the portion of the laser beam, the lower an intensity of the beam at a portion TPA detector 130. In a third example, the closer the focal point is to surface 112, the higher an intensity of the beam at a portion TPA detector 130. In a fourth example, the smaller a diameter of the at least the portion of the laser beam, the higher an intensity of the beam at a portion TPA detector 130. In another example, when the focal point is at surface 112, a diameter at TPA detector 130 may be at a minimum, and an intensity may be at a maximum.

As illustrated, computer system 152 may be communicatively coupled to TPA detector 130. As shown, computer system 152 may be communicatively coupled to laser 120. As illustrated, computer system 152 may be communicatively coupled to beam expander 141. As shown, computer system 152 may be communicatively coupled to scanner 144. In one example, computer system 152 may receive information from one or more of laser 120, TPA detector 130, beam expander 141, and scanner 144, among others. In another example, computer system 152 may provide information to one or more of laser 120, TPA detector 130, beam expander 141, and scanner 144, among others. Computer system 152 may provide control information to one or more of laser 120, TPA detector 130, beam expander 141, and scanner 144, among others.

Computer system 152 may determine if a focal point of a laser beam is calibrated in response to intensity measurements from TPA detector 130. Computer system 152 may determine if an intensity is a maximum intensity. The maximum intensity may be the maximum of intensities may be measured at different positions of a focal point. The maximum intensity may be measured or calculated prior to a calibration session, so computer system 152 may determine if the intensity measured during the calibration session is at a maximum. If the intensity is the maximum intensity, computer system 152 may determine that the focal point is at surface 112. If the intensity is not the maximum intensity, computer system 152 may adjust focusing optics 140 to direct a focal point to a different point of the Z-axis. Computer system 152 may generate, from one or more TPA detector signals, a graph that may represent intensities of the at least the portion of the laser beam. For example, the one or more TPA detector signals may be or include data.

Figure 1B:
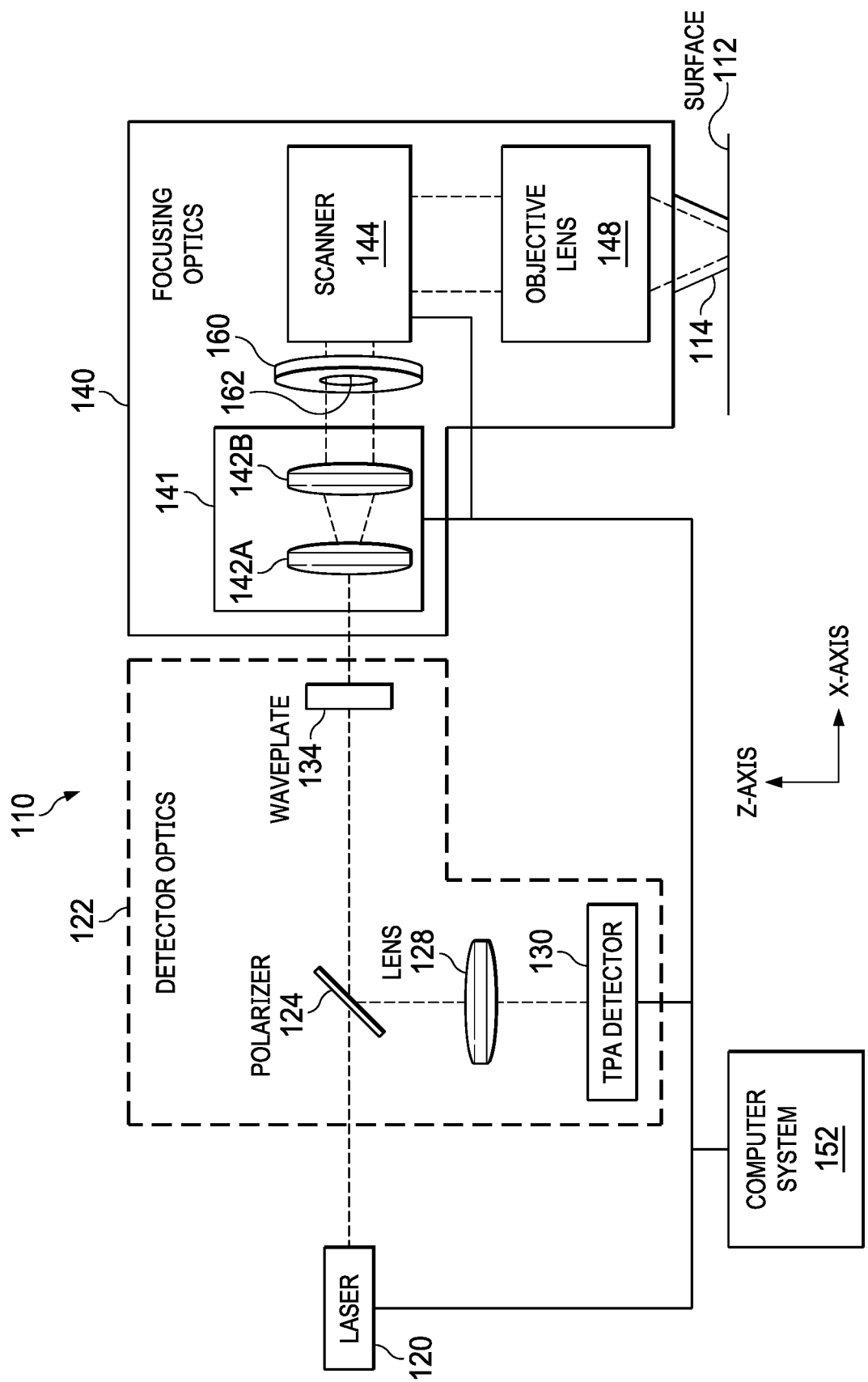
FIG. 1B illustrates another example of an optical system.

Turning now to FIG. 1B, another example of an optical system is illustrated. As shown, optical system 110 may include a diaphragm 160. As illustrated, diaphragm 160 may include an aperture 162. As shown, computer system 152 may be communicatively coupled to diaphragm 160. Computer system 152 may provide control information to diaphragm 160, among others. For example, computer system 152 may provide, to diaphragm 160, control information that indicates a diameter of aperture 162. A diameter of aperture 162 may permit light to travel through diaphragm 160. For example, diaphragm 160 may prevent light from traveling through one or more areas of diaphragm 160 other than aperture 162. Although not specifically illustrated, computer system 152 may not be communicatively coupled to diaphragm 160. In one example, a diameter of aperture 162 may be fixed. In another example, a diameter of aperture 162 may be adjusted by a person.

Figure 2A:
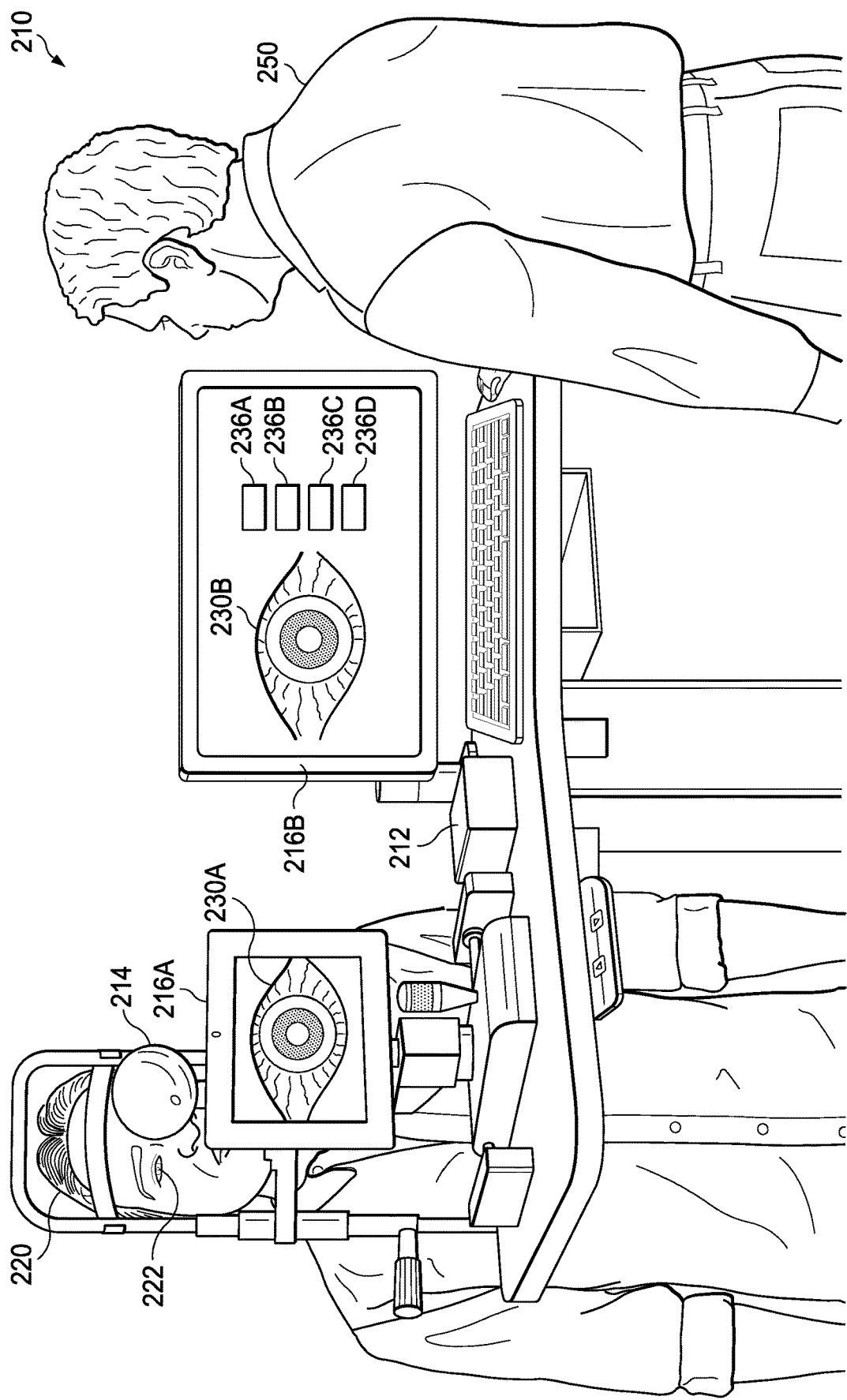
FIG. 2A illustrates an example of a medical system.

Turning now to FIG. 2A, an example of a medical system is illustrated. As shown, a medical system 210 may be utilized with a patient 220. As illustrated, medical system 210 may include a computer system 212. Computer system 212 may be communicatively coupled to displays 216A and 216B. Computer system 212 may be communicatively coupled to a biometry device 214. In one example, biometry device 214 may include one or more cameras. In another example, biometry device 214 may include a three-dimensional scanner. Biometry device 214 may be utilized in biometry of an eye 222 of patient 220. As shown, display 216A may display an image 230A associated with eye 222 of patient 220. As illustrated, display 216B may display an image 230B associated with eye 222 of patient 220.

Computer system 212 may determine eye recognition information. For example, the eye recognition information may include biometry information associated with eye 222 of patient 220. The biometry information associated with eye 222 may include one or more of a pattern of blood vessels of a sclera of eye 222, a structure of an iris of eye 222, a position of a structure of an iris of eye 222, a distance measurement of a cornea of eye 222 to a lens of eye 222, a distance measurement of a lens of eye 222 to a retina of eye 222, a corneal topography of eye 222, a retinal pattern of eye 222, and a wavefront measurement, among others.

As shown, display 216B may display display areas 236A-236D. In one example, a display area 236 may display a distance measurement of a cornea of eye 222 to a lens of eye 222, a distance measurement of a lens of eye 222 to a retina of eye 222, a position of a structure of an iris 234, corneal topography information, or wavefront measurement information, among other biometry information associated with eye 222. In another example, a display area 236 may display any information associated with patient 220.

A person 250 may operate medical system 210. For example, person 250 may be medical personnel. Person 250 may enter identification information associated with patient 220 into computer system 212. The identification information associated with patient 220 may include one or more of a name of patient 220, an address of patient 220, a telephone number of patient 220, a government issued identification number of patient 220, a government issued identification string of patient 220, and a date of birth of patient 220, among others.

Person 250 may provide medical procedure information, associated with patient 220, to computer system 212. The medical procedure information may be associated with a medical procedure. The medical procedure information may be associated identification information associate with patient 220. Computer system 212 may store the medical procedure information. For example, computer system 212 may store the medical procedure information for later utilization. The medical procedure information may be associated with a surgery. For example, the medical procedure information may be retrieved before the surgery. The medical procedure information may be utilized during a medical procedure. For example, the medical procedure may include a surgery.

Figure 2B:
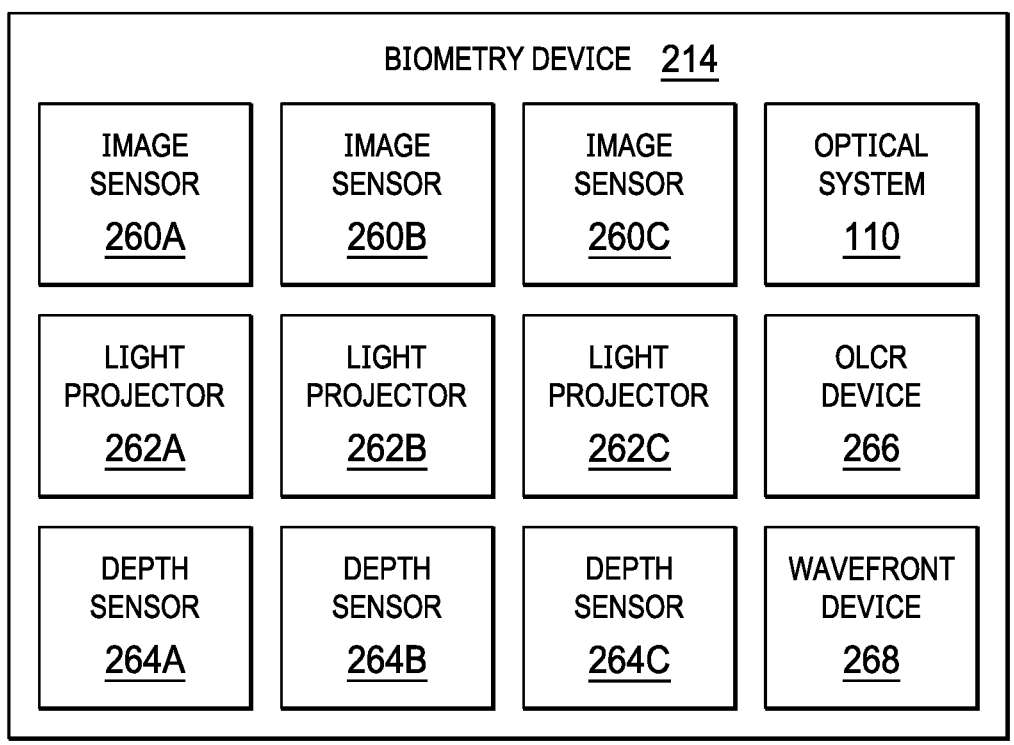
FIG. 2B illustrates an example of a biometry device.

Turning now to FIG. 2B, an example of a biometry device is illustrated. As shown, biometry device 214 may include image sensors 260A-260C. For example, an image sensor 260 may include a camera. A camera may include a one or more digital image sensors. In one example, a digital image sensor may include a charge-coupled device (CCD). In another example, a digital image sensor may include a complementary metal-oxide-semiconductor (CMOS). The camera may transform light into digital data. The camera may utilize a Bayer filter mosaic. For example, the camera may utilize a Bayer filter mosaic in combination with an optical anti-aliasing filter. A combination of the Bayer filter mosaic in combination with the optical anti-aliasing filter may reduce aliasing due to reduced sampling of different primary-color images. The camera may utilize a demosaicing process. For example, the demosaicing process may be utilized to interpolate color information to create a full array of red, green, and blue (RGB) image data.

As illustrated, biometry device 214 may include light projectors 262A-262C. In one example, a light projector 262 may project visible light. In another example, a light projector 262 may project infrared light. A light projector 262 may project circles and/or dots onto an eye of a patient. An image sensor 260 may receive reflections of the circles and/or the dots that were projected onto the eye of the patient. A computer system may determine one or more locations and/or one or more templates associated with the eye of the patient based at least on the reflections of the circles and/or the dots that were projected onto the eye of the patient. As shown, biometry device 214 may include depth sensors 264A-264C. A depth sensor 264 may include a light projector 262. A depth sensor 264 may include an optical sensor. As illustrated, biometry device 214 may include an optical low coherence reflectometer (OLCR) device 266. As shown, biometry device 214 may include a wavefront device 268.

Wavefront device 268 may include one or more of a light source and a wavefront sensor, among others. A light source may provide a first light wave to eye 222. A wavefront sensor may receive a first perturbed light wave, based at least on the first light wave, from eye 222. In one example, wavefront device 268 may determine first optical corrections based at least on the first perturbed light. In another example, a computer system may determine first optical corrections based at least on the first perturbed light. Wavefront device 268 may provide data, based at least on the first perturbed light wave, to a computer system. For example, the computer system may determine first optical corrections based at least on the data from wavefront device 268.

Any two or more of an image sensor 260, a light projector 262, a depth sensor 264, an OLCR device 266, and a wavefront device 268 may be combined. One or more of image sensors 260A-260C, one or more of light projectors 262A-262C, one or more of depth sensors 264A-264C, OLCR device 266, and/or wavefront device 268, among others, may produce data that may be utilized by a computer system. As illustrated, biometry device 214 may include an optical system 110.

Figure 3A:
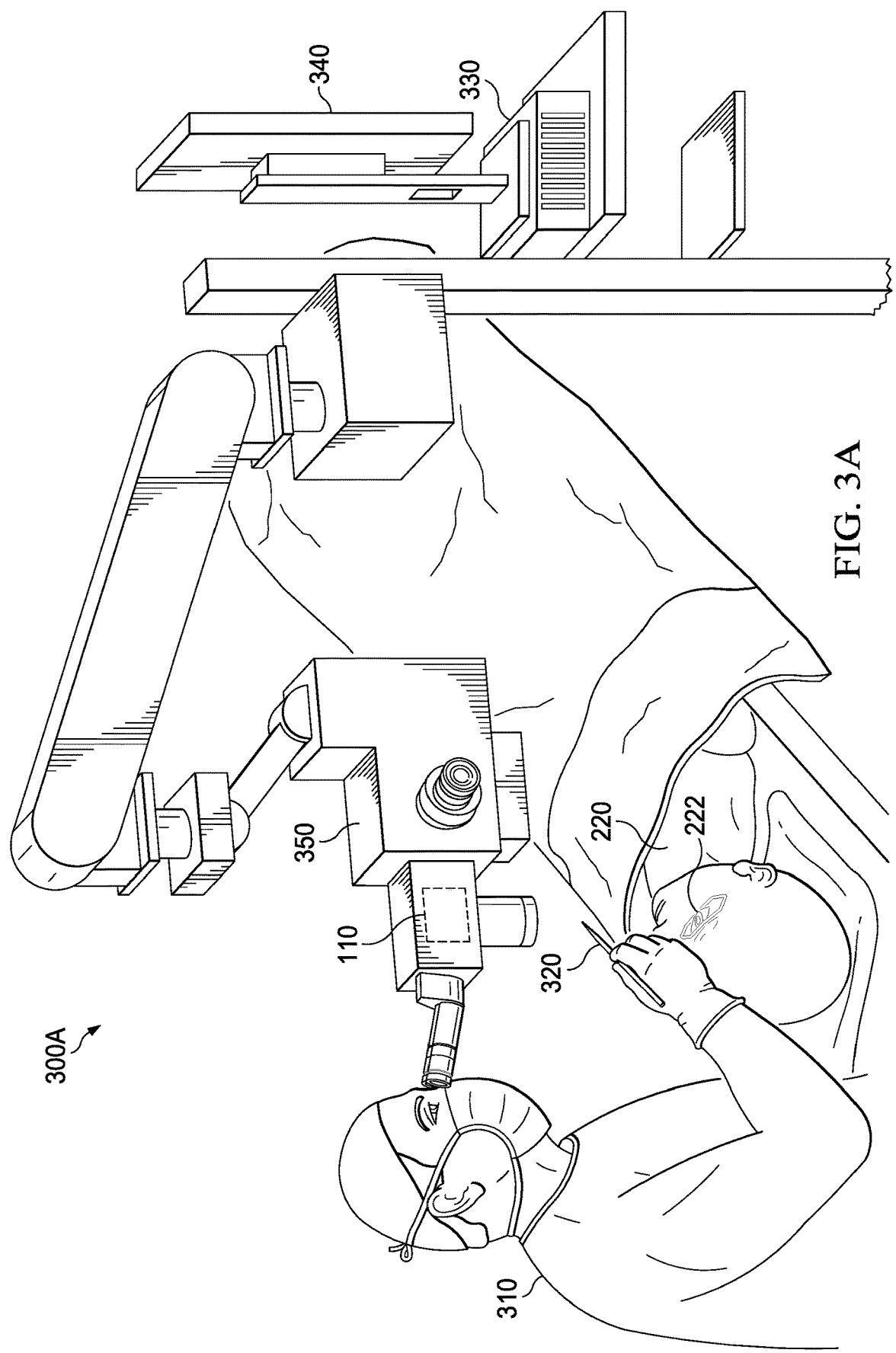
FIG. 3A illustrates a second example of a medical system.

Turning now to FIG. 3A, a second example of a medical system is illustrated. As shown, a surgeon 310 may utilize surgical tooling equipment 320. In one example, surgeon 310 may utilize surgical tooling equipment 320 in a surgery involving eye 222 of patient 220. A medical system 300A may include an ophthalmic surgical tool tracking system. As illustrated, medical system 300A may include a computer system 330, a display 340, and a microscope integrated display (MID) 350.

Computer system 330 may receive image frames captured by one or more image sensors. For example, computer system 330 may perform various image processing on the one or more image frames. Computer system 330 may perform image analysis on the one or more image frames to identify and/or extract one or more images of surgical tooling equipment 320 from the one or more image frames. Computer system 330 may generate a graphical user interface (GUI), which may overlay the one or more image frames. For example, the GUI may include one or more indicators and/or one or more icons, among others. The one or more indicators may include surgical data, such as one or more positions and/or one or more orientations. The one or more indicators may include one or more warnings. The GUI may be displayed by display 340 and/or MID 350 to surgeon 310 and/or other medical personnel.

Computer system 330, display 340, and MID 350 may be implemented in separate housings communicatively coupled to one another or within a common console or housing. A user interface may be associated with one or more of computer system 330, display 340, and MID 350, among others. For example, a user interface may include one or more of a keyboard, a mouse, a joystick, a touchscreen, an eye tracking device, a speech recognition device, a gesture control module, dials, and/or buttons, among other input devices. A user (e.g., surgeon 310 and/or other medical personnel) may enter desired instructions and/or parameters via the user interface. For example, the user interface may be utilized in controlling one or more of computer system 330, display 340, and MID 350, among others. As illustrated, MID 350 may include an optical system 110.

Figure 3B:
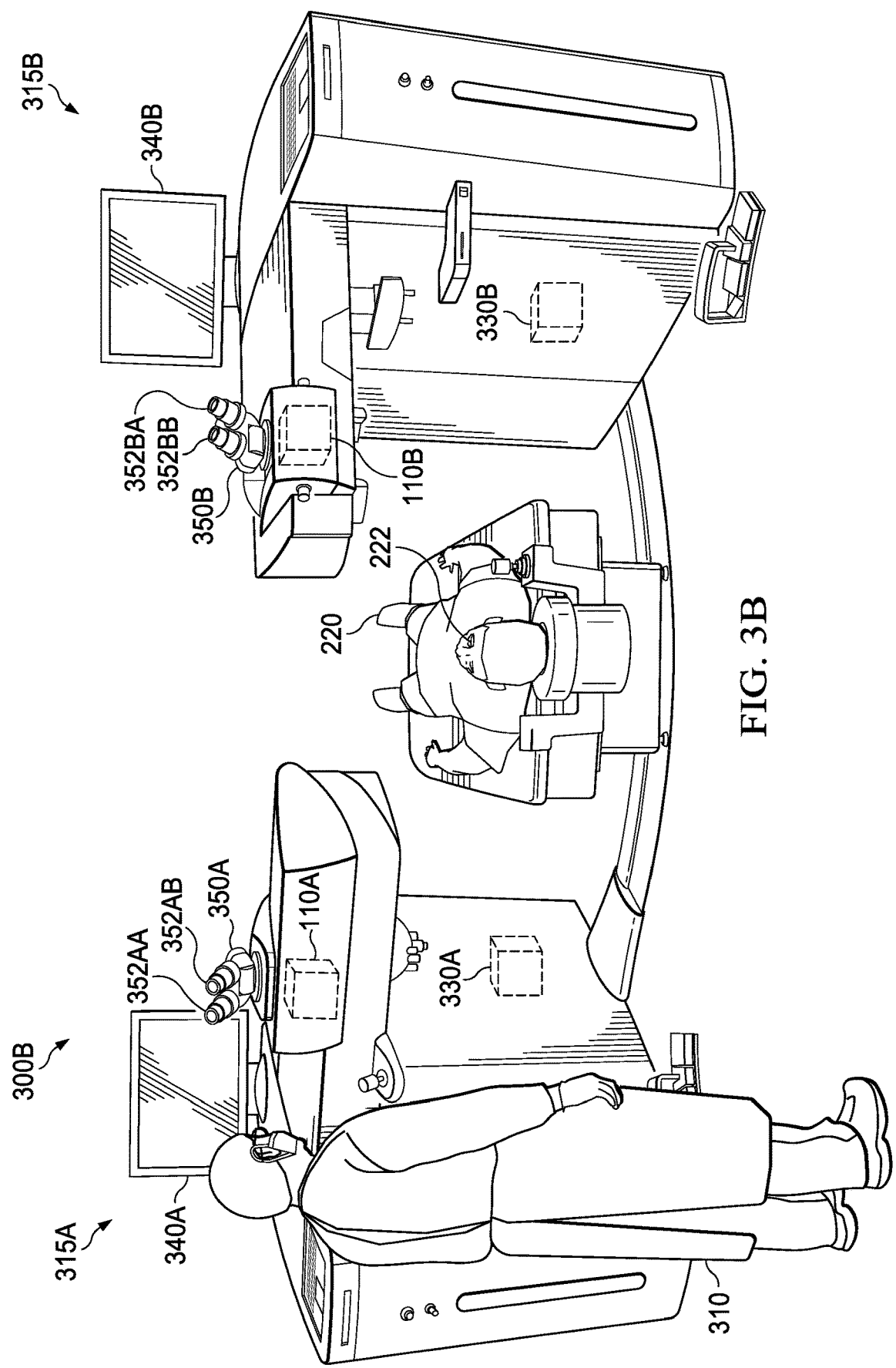
FIG. 3B illustrates a third example of a medical system.

Turning now to FIG. 3B, a third example of a medical system is illustrated. As shown, a surgeon 310 may utilize a system 300B. For example, surgeon 310 may utilize system 300B in a surgery involving eye 222 of patient 220. System 300B may include multiple systems. As shown, system 300B may include a cutting system 315A. For example, surgeon 310 may utilize system 315A in cutting eye 222. Eye 222 may include a flap in a cornea of an eye of patient 220. As illustrated, system 300B may include a shaping system 315B. For example, surgeon 310 may utilize shaping system 315B in performing ablation on an interior part of the cornea of eye 222.

As shown, system 315A may include a display 340A. As illustrated, system 315A may include a MID 350A. As illustrated, MID 350A may include eye pieces 352AA and 352AB. An eye piece 352A may refer to an eye piece 352AA or to an eye piece 352BA. An eye piece 352B may refer to an eye piece 352AB or to an eye piece 352BB. System 315A may include one or more of image sensors 260A-260C, one or more of light projectors 262A-262C, one or more of depth sensors 264A-264C, OLCR device 266, wavefront device 268, and/or an optical system 110A, among others. As illustrated, system 315B may include a display 340B. As shown, system 315B may include a MID 350B. As illustrated, MID 350B may include eye pieces 352BA and 352BB. System 315B may include one or more of image sensors 260A-260C, one or more of light projectors 262A-262C, one or more of depth sensors 264A-264C, OLCR device 266, and/or wavefront device 268, among others. As shown, system 315B may include an optical system 110B.

System 315A may include a laser, such as a femtosecond laser, which may use short laser pulses to ablate a series of small portions of corneal tissue to form a flap that may be lifted up to expose an interior part of the cornea. The flap may be planned and cut using one or both of cutting device displays 340A and 350A, along with control devices and a computer system 330A. As shown, system 315A may include computer system 330A. For example, computer system 330A may be communicatively coupled to one or more of image sensors 260A-260C, one or more of light projectors 262A-262C, one or more of depth sensors 264A-264C, OLCR device 266, wavefront device 268, and/or optical system 110A, among others, of system 315A. As illustrated, system 315B may include computer system 330B. For example, computer system 330B may be communicatively coupled to one or more of image sensors 260A-260C, one or more of light projectors 262A-262C, one or more of depth sensors 264A-264C, OLCR device 266, wavefront device 268, and/or optical system 110B among others, of system 315B.

Systems 315A and 315B may be physically separated as shown in FIG. 3B. Patient 220 may be moved between systems 315A and 315B. Alternatively, patient 220 may remain stationary and systems 315A and 315B may be moved to patient 220. Systems 315A and 315B may be physically combined into a single unitary device, such that neither the device nor patient 220 is repositioned when switching between systems 315A and 315B.

System 300B may include one or more control devices for controlling systems 315A and 315B. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 300B may include at least one computer system configured to generate an image presented on at least one of displays 340A, 350A, 340B, and 350B, among others. For example, the at least one computer system may include one or more of computer systems 330A and 330B. One or more of computer systems 330A and 330B may be communicatively coupled to observational devices, such as a microscope, a camera, an optical coherence tomography (OCT) device or display, or another device able to measure the position of the eye undergoing surgery. One or more of computer systems 330A and 330B may be communicatively coupled to one or more of the control devices.

In one example, cutting device computer system 330A: i) may be communicatively coupled to observational devices that observe the eye when patient 220 is positioned with system 315A, ii) may provide graphical information regarding the planned flap location and the planned area of ablation to one or more of displays 340A and 350A, and iii) may be communicatively coupled to one or more control devices of system 315A. In a second example, shaping device computer 330B: i) may be communicatively coupled to observational devices that observe the eye when patient 220 is positioned with a shaping device, ii) may provide graphical information regarding the planned flap location and the planned area of ablation to one or more of displays 340B and 350B, and iii) may be communicatively coupled to one or more control devices of system 315B. In another example, a computer system may include the properties and/or the attributes described above with respect to one or more of computer systems 330A and 330B, among others.

A computer system of a system 300 may be communicatively coupled to another part of system 300 in a wired fashion or in a wireless fashion. One of more of computer systems of system 300 may be communicatively coupled to a database, stored locally, on a remote computer system or a remote data center, or both, that store patient data, treatments plans, and/or other information associated with medical treatments and/or system 300. In one example, the database may include a relational database. In a second example, the database may include a graph database. In another example, the database may include a "Not Only SQL" (NoSQL) database.

System 300 may enter information regarding patient 220 and the treatment to be performed on patient 220 or actually performed on patient 220. System 300 may allow a user to enter and view information regarding patient 220 and the treatment to be performed on patient 220. Such data may include information about patient 220, such as identifying information, a medical history of patient 220, and/or information about eye 222 being treated, among others. Such data may include information about the treatment plans, such as the shape and location of a corneal cut and/or a shape and location of ablation, among others.

Figure 3C:
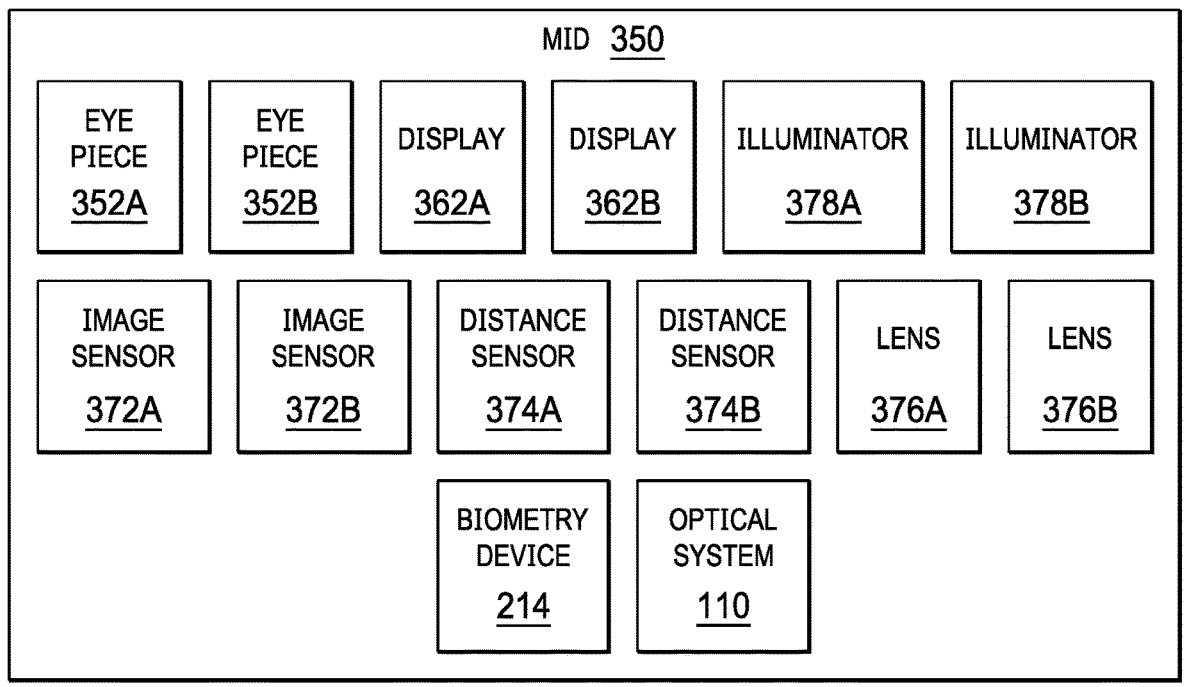
FIG. 3C illustrates an example of a microscope integrated display and examples of surgical tooling equipment.
Figure 3C:
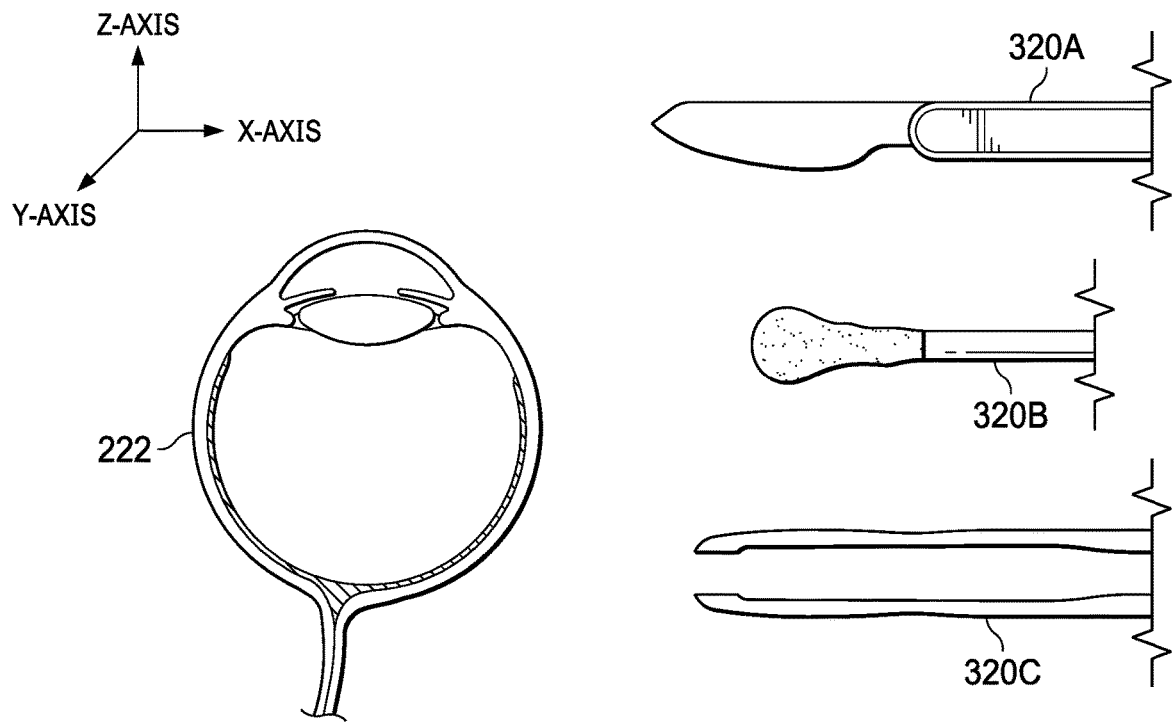

Turning now to FIG. 3C, an example of a microscope integrated display and examples of surgical tooling equipment are illustrated. As shown, surgical tooling equipment 320A may be or include a scalpel. As illustrated, surgical tooling equipment 320B may be or include a Q-tip. As shown, surgical tooling equipment 320C may be or include tweezers. Other surgical tooling equipment that is not specifically illustrated may be utilized with one or more systems, one or more processes, and/or one or more methods described herein.

As an example, surgical tooling equipment 320 may be marked with one or more patterns. The one or more patterns may be utilized in identifying surgical tooling equipment 320. The one or more patterns may include one or more of a hash pattern, a stripe pattern, and a fractal pattern, among others. As another example, surgical tooling equipment 320 may be marked with a dye and/or a paint. The dye and/or the paint may reflect one or more of visible light, infrared light, and ultraviolet light, among others. In one example, an illuminator 378 may provide ultraviolet light, and image sensor 372 may receive the ultraviolet light reflected from surgical tooling equipment 320. Computer system 330 may receive image data, based at least on the ultraviolet light reflected from surgical tooling equipment 320, from image sensor 372 and may utilize the image data, based at least on the ultraviolet light reflected from surgical tooling equipment 320, to identify surgical tooling equipment 320 from other image data provided by image sensor 372. In another example, an illuminator 378 may provide infrared light, and image sensor 372 may receive the infrared light reflected from surgical tooling equipment 320. Computer system 330 may receive image data, based at least on the infrared light reflected from surgical tooling equipment 320, from image sensor 372 and may utilize the image data, based at least on the infrared light reflected from surgical tooling equipment 320, to identify surgical tooling equipment 320 from other image data provided by image sensor 372.

As illustrated, MID 350 may include eye pieces 352A and 352B. As shown, MID 350 may include displays 362A and 362B. Surgeon 310 may look into eye pieces 352A and 352B. In one example, display 362A may display one or more images via eye piece 352A. A left eye of surgeon 310 may utilize eye piece 352A. In another example, display 362B may display one or more images via eye piece 352B. A right eye of surgeon 310 may utilize eye piece 352B. Although MID 350 is shown with multiple displays, MID 350 may include a single display 362. For example, the single display 362 may display one or more images via one or more of eye pieces 352A and 352B. MID 350 may be implemented with one or more displays 362.

As shown, MID 350 may include image sensors 372A and 372B. In one example, image sensors 372A and 372B may acquire images. In a second example, image sensors 372A and 372B may include cameras. In another example, an image sensor 372 may acquire images via one or more of visible light, infrared light, and ultraviolet light, among others. One or more image sensors 372A and 372B may provide data of images to computer system 330. Although MID 350 is shown with multiple image sensors, MID 350 may include a single image sensor 372. MID 350 may be implemented with one or more image sensors 372.

As illustrated, MID 350 may include distance sensors 374A and 374. For example, a distance sensor 374 may determine a distance to surgical tooling equipment 320. Distance sensor 374 may determine a distance associated with a Z-axis. Although MID 350 is shown with multiple image sensors, MID 350 may include a single distance sensor 374. In one example, MID 350 may be implemented with one or more distance sensors 374. In another example, MID 350 may be implemented with no distance sensor.

As shown, MID 350 may include lenses 376A and 376B. Although MID 350 is shown with multiple lenses 376A and 376B, MID 350 may include a single lens 376. MID 350 may be implemented with one or more lenses 376. As illustrated, MID 350 may include illuminators 378A and 378B. For example, an illuminator 378 may provide and/or produce one or more of visible light, infrared light, and ultraviolet light, among others. Although MID 350 is shown with multiple illuminators, MID 350 may include a single illuminator 378. MID 350 may be implemented with one or more illuminators 378. MID 350 may include one or more structures and/or one or more functionalities as those described with reference to biometry device 214. In one example, MID 350 may include OLCR device 266. In another example, MID 350 may include wavefront device 268. MID 350 may include a biometry device 214. MID 350 may include an optical system 110.

Figure 3D:
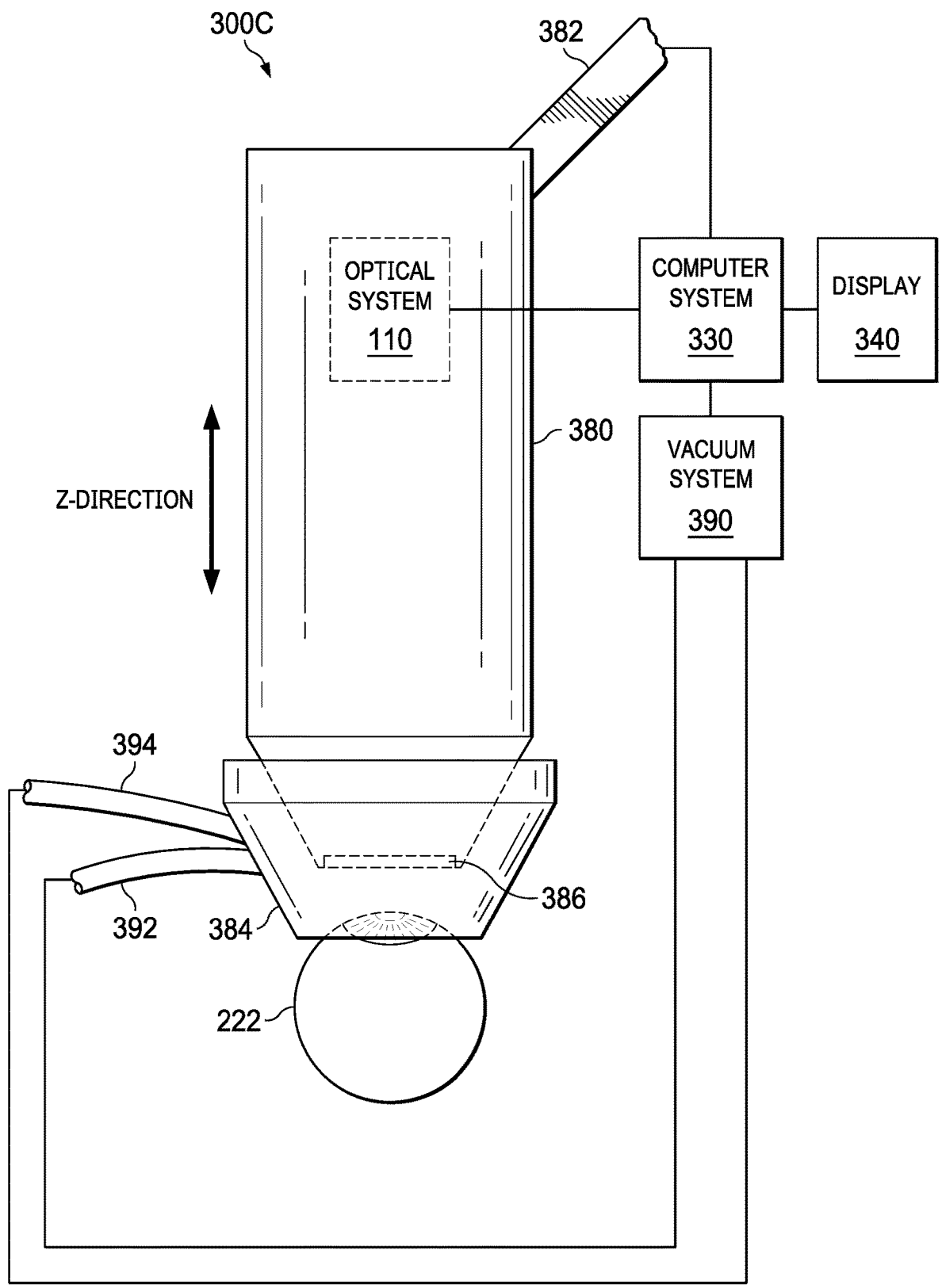
FIG. 3D illustrates another example of a medical system.

Turning now to FIG. 3D, another example of a medical system is illustrated. As shown, a medical system 300C may include a suction cone 380. For example, suction cone 380 may be or include an aplenation cone. As illustrated, suction cone 380 may include an optical system 110. As shown, a computer system 330 may be coupled to a control device 382 of suction cone 380. For example, computer system 330 may control suction cone 380 via control device 382. After a suction ring 384 is docked with an eye 222, suction cone 380 may be docked with suction ring 384. As illustrated, suction cone 380 may include a lens 386. Although lens 386 is illustrated as flat or planar, lens 386 may include concave shape and/or may include convex shape. If lens 386 is planar, lens 386 may be referred to as an aplenation plane.

As illustrated, medical system 300C may include a vacuum system 390. As shown, vacuum system 390 may be communicatively coupled to computer system 330. For example, computer system 330 may control vacuum system 390. Vacuum system 390 may create one or more low pressures via one or more of lines 392 and 394. For example, vacuum system 390 may create one or more low pressures via line 394 to adhere and/or seal a suction ring 384 to an eye 222 of a patient. As shown, medical system 300C may include lines 392 and 394 and suction ring 384.

Figure 4:
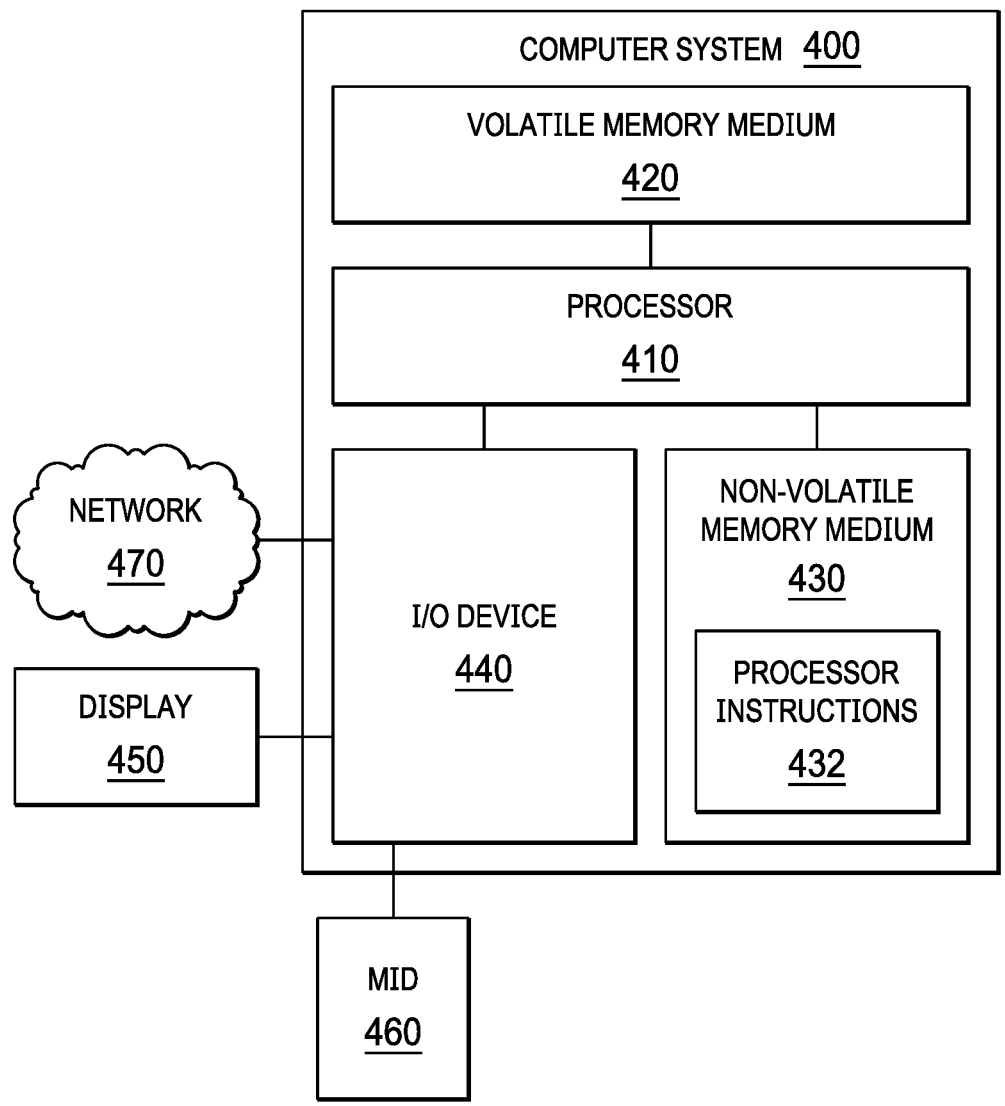
FIG. 4 illustrates an example of a computer system.

Turning now to FIG. 4, an example of a computer system is illustrated. As shown, a computer system 400 may include a processor 410, a volatile memory medium 420, a non-volatile memory medium 430, and an input/output (I/O) device 440. As illustrated, volatile memory medium 420, non-volatile memory medium 430, and I/O device 440 may be communicatively coupled to processor 410.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 430 may include processor instructions 432. Processor instructions 432 may be executed by processor 410. In one example, one or more portions of processor instructions 432 may be executed via non-volatile memory medium 430. In another example, one or more portions of processor instructions 432 may be executed via volatile memory medium 420. One or more portions of processor instructions 432 may be transferred to volatile memory medium 420.

Processor 410 may execute processor instructions 432 in implementing at least a portion of one or more systems, one or more flow charts, one or more processes, and/or one or more methods described herein. For example, processor instructions 432 may be configured, coded, and/or encoded with instructions in accordance with at least a portion of one or more systems, one or more flowcharts, one or more methods, and/or one or more processes described herein. Although processor 410 is illustrated as a single processor, processor 410 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 410 may include any suitable system, device, or apparatus operable to interpret and execute program instructions, process data, or both stored in a memory medium and/or received via a network. Processor 410 further may include one or more microprocessors, microcontrollers, digital signal processors (DSPs), application specific integrated circuits (ASICs), or other circuitry configured to interpret and execute program instructions, process data, or both.

I/O device 440 may include any instrumentality or instrumentalities, which allow, permit, and/or enable a user to interact with computer system 400 and its associated components by facilitating input from a user and output to a user. Facilitating input from a user may allow the user to manipulate and/or control computer system 400, and facilitating output to a user may allow computer system 400 to indicate effects of the user's manipulation and/or control. For example, I/O device 440 may allow a user to input data, instructions, or both into computer system 400, and otherwise manipulate and/or control computer system 400 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 440 may include one or more busses, one or more serial devices, and/or one or more network interfaces, among others, that may facilitate and/or permit processor 410 to implement at least a portions of one or more systems, processes, and/or methods described herein. In one example, I/O device 440 may include a storage interface that may facilitate and/or permit processor 410 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 440 may include a network interface that may facilitate and/or permit processor 410 to communicate with a network. I/O device 440 may include one or more of a wireless network interface and a wired network interface. In a third example, I/O device 440 may include one or more of a peripheral component interconnect (PCI) interface, a PCI Express (PCIe) interface, a serial peripheral interconnect (SPI) interface, and an inter-integrated circuit ($I^2C$) interface, among others. In a fourth example, I/O device 440 may include circuitry that may permit processor 410 to communicate data with one or more sensors. In a fifth example, I/O device 440 may facilitate and/or permit processor 410 to communicate data with one or more of a display 450 and a MID 460, among others. In another example, I/O device 440 may facilitate and/or permit processor 410 to communicate data with an imaging device 470. As illustrated, I/O device 440 may be coupled to a network 480. For example, I/O device 440 may include a network interface.

Network 480 may include a wired network, a wireless network, an optical network, or a combination of the foregoing, among others. Network 480 may include and/or be coupled to various types of communications networks. For example, network 480 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

A computer system described herein may include one or more structures and/or one or more functionalities as those described with reference to computer system 400. In one example, computer system 152 may include one or more structures and/or one or more functionalities as those described with reference to computer system 400. In a second example, computer system 212 may include one or more structures and/or one or more functionalities as those described with reference to computer system 400. In a third example, computer system 330 may include one or more structures and/or one or more functionalities as those described with reference to computer system 400. In another example, a computer system of MID 350 may include one or more structures and/or one or more functionalities as those described with reference to computer system 400.

Figure 5:
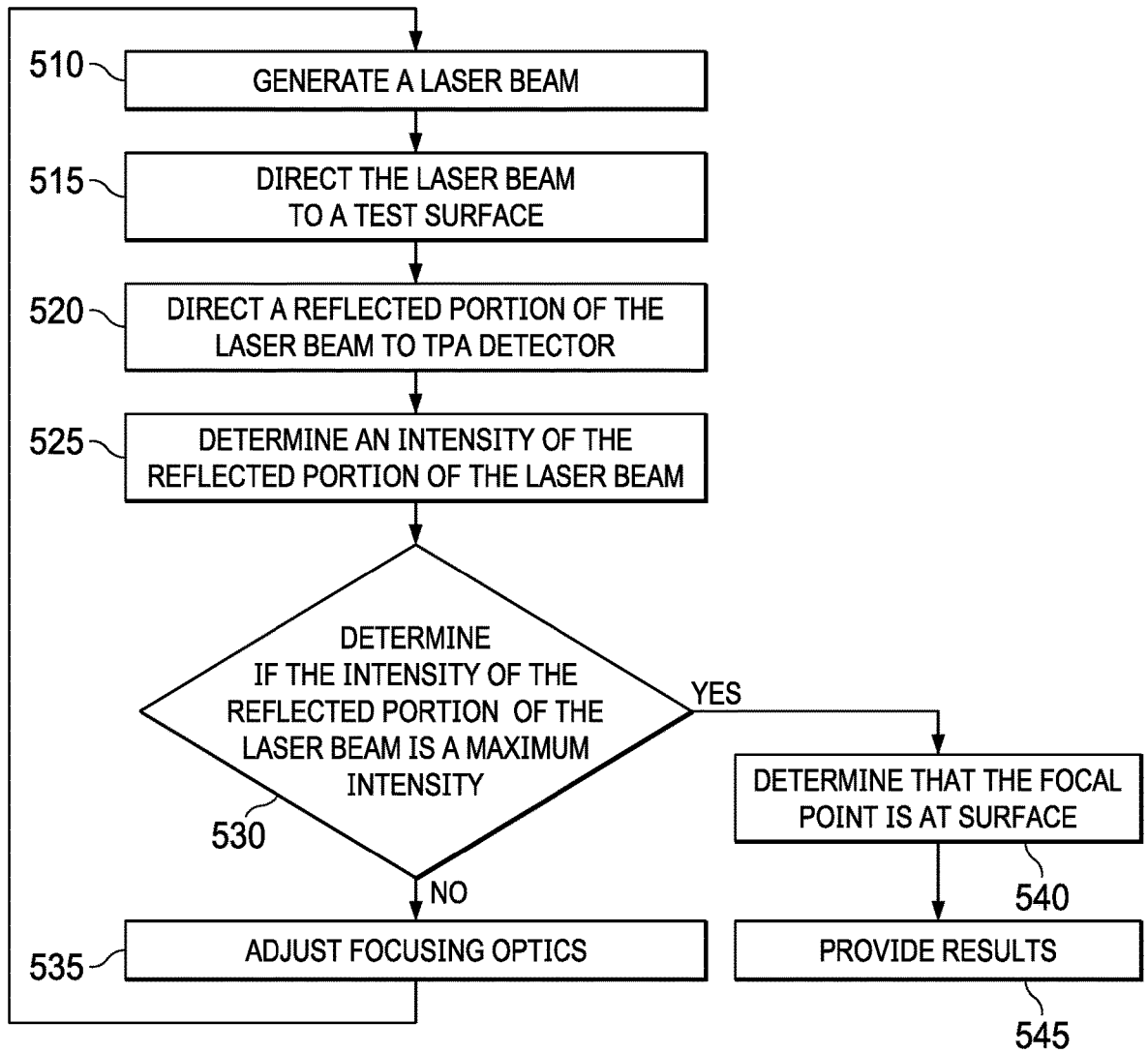
FIG. 5 illustrates an example of a method of operating an optical system.

Turning now to FIG. 5, an example of a method of operating an optical system is illustrated. At 510, a laser beam may be generated. For example, laser 120 may generate a laser beam. Computer system 152 may provide control information, that indicates generating a laser beam, to laser 120. For example, laser 120 may receive the control information from computer system 152 and generate the laser beam in accordance with the control information.

At 515, the laser beam may be directed to a test surface. For example, focusing optics 140 may direct the laser beam to surface 112. Focusing optics 140 may reflect a portion of the laser beam. A remainder of the laser beam may travel to surface 112. At 520, a reflected portion of the laser beam may be directed to TPA detector 130. For example, detector optics 122 may direct the reflected portion of the laser beam to TPA detector 130. The reflected portion of the laser beam may be reflected from surface 112.

At 525, an intensity of the reflected portion of the laser beam may be determined. For example, TPA detector 130 may determine an intensity of the reflected portion of the laser beam. TPA detector 130 may transform the intensity of the reflected portion of the laser beam into digital data that indicates the intensity of the reflected portion of the laser beam. TPA detector 130 may provide the digital data that indicates the intensity of the reflected portion of the laser beam to computer system 152. Computer system 152 may receive the digital data that indicates the intensity of the reflected portion of the laser beam.

At 530, it may be determined if the intensity of the reflected portion of the laser beam is a maximum intensity. The intensity of the reflected portion of the laser beam may be a peak intensity as photons of the reflected portion of the laser beam may behave as a wave. Computer system 152 may determine, from the digital data that indicates the intensity of the reflected portion of the laser beam, if the intensity of the reflected portion of the laser beam is a maximum intensity. Determining if the intensity of the reflected portion of the laser beam is a maximum intensity may include comparing the intensity of the reflected portion of the laser beam with other one or more intensities of repetitive other reflected portions of the laser beam. For example, computer system 152 may store and/or access the other one or more intensities via memory medium.

If the signal is not at the maximum intensity, focusing optics 140 may be adjusted, at 535. For example, computer system 152 may adjust focusing optics 140. Computer system 152 may provide, to focusing optics 140, control information that indicates at least one adjustment of focusing optics 140. For example, computer system 152 may provide, to beam expander 141, control information that indicates at least one adjustment of one or more of lenses 142A and 142B. Adjusting focusing optics 140 may direct a focal point of the laser beam to a different location with respect to the Z-axis. For example, adjusting focusing optics 140 may direct a focal point of the laser beam toward or away from surface 112. The method may proceed to 510.

If the signal is at the maximum, it may be determined that the focal point is at surface 112, at 540. For example, computer system 152 may determine that the focal point is at surface 112. Interpolation may be utilized to refine a position of surface 112. At 545, results may be provided. For example, computer system 152 may provide results. Providing the results may include one or more of displaying the results via a display, printing the results via a printer, storing the results to a memory medium, and sending the result to a communication network, among others.

Figure 6:
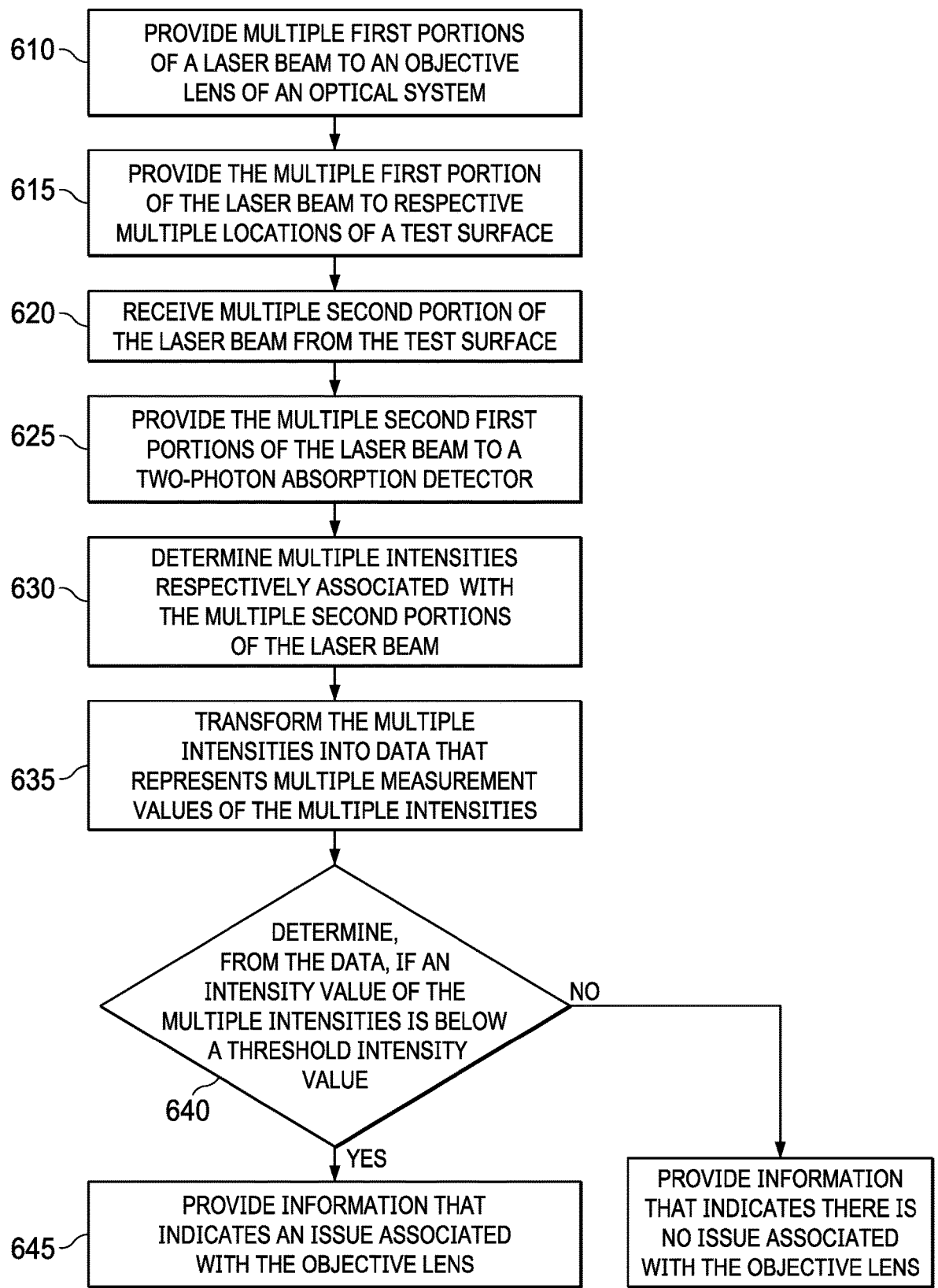
FIG. 6 illustrates an example of a method of determining if an objective lens is associated with an issue.

Turning now to FIG. 6, an example of a method of determining if an objective lens is associated with an issue. At 610, multiple first portions of a laser beam may be provided to an objective lens of an optical system. Providing the multiple first portions of the laser beam to the objective lens may include directing the multiple first portions of the laser beam to the objective lens. For example, one or more of polarizer 124, waveplate 134, beam expander 141, and scanner 144 may direct the multiple first portions of the laser beam to objective lens 148.

Figure 7A:
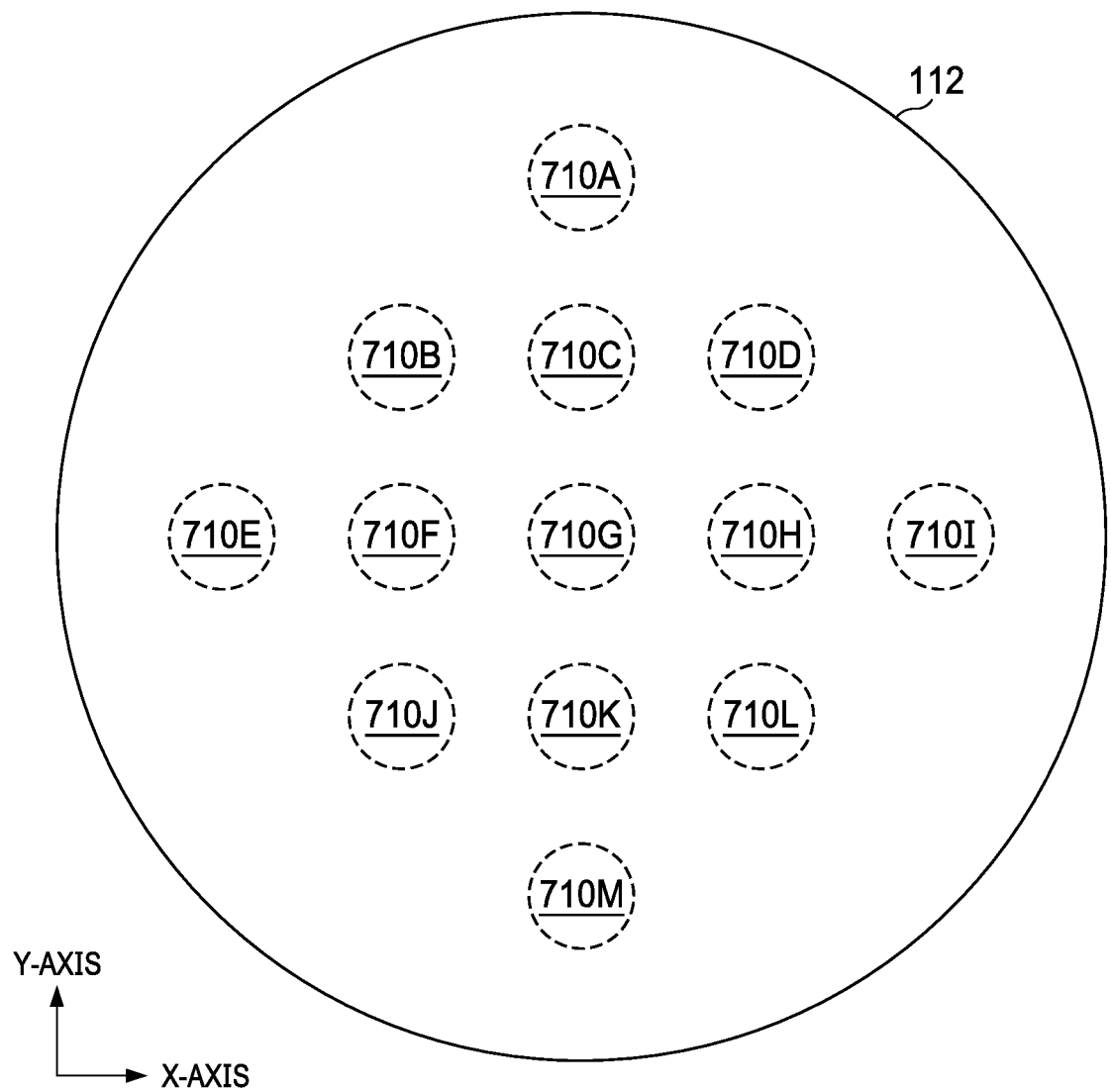
FIG. 7A illustrates an example of a test surface and multiple locations.
Figure 7B:
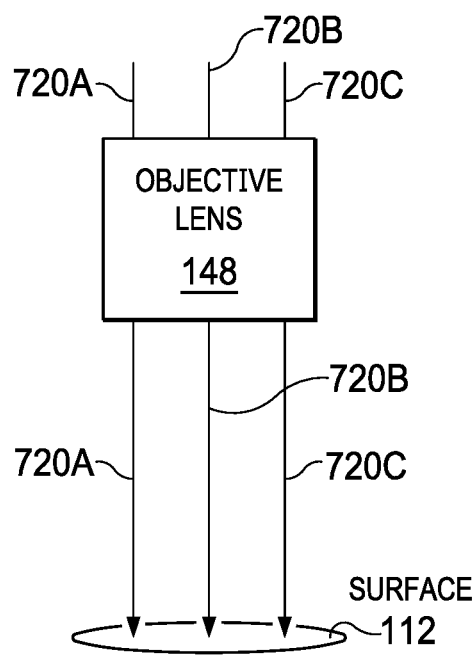
FIG. 7B illustrates an example of an objective lens providing portions of a laser beam to a test surface.
Figure 7C:
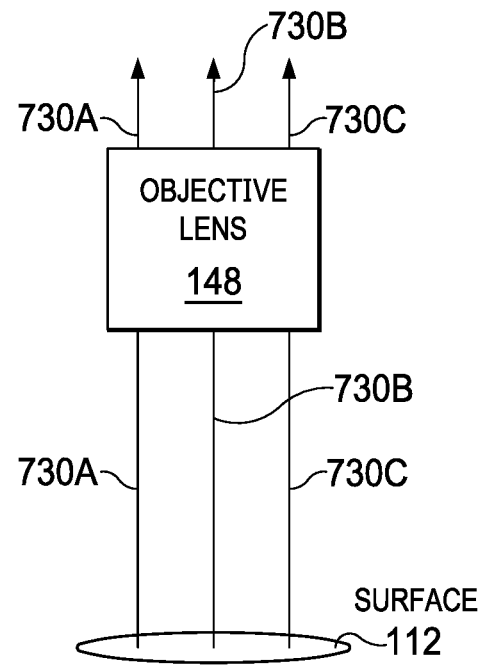
FIG. 7C illustrates an example of an objective lens receiving portions of a laser beam reflected off a test surface.
Figure 7D:
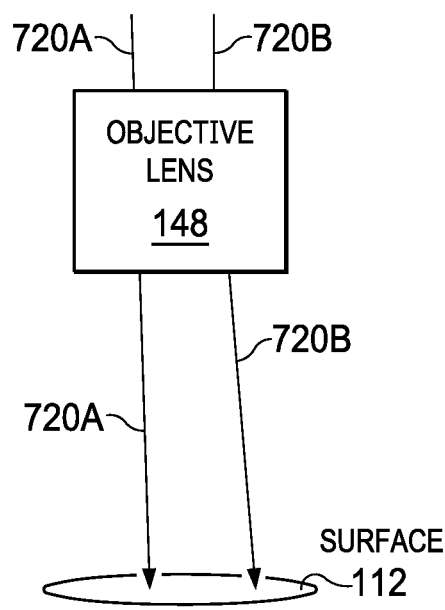
FIG. 7D illustrates another example of an objective lens providing portions of a laser beam to a test surface.
Figure 7E:
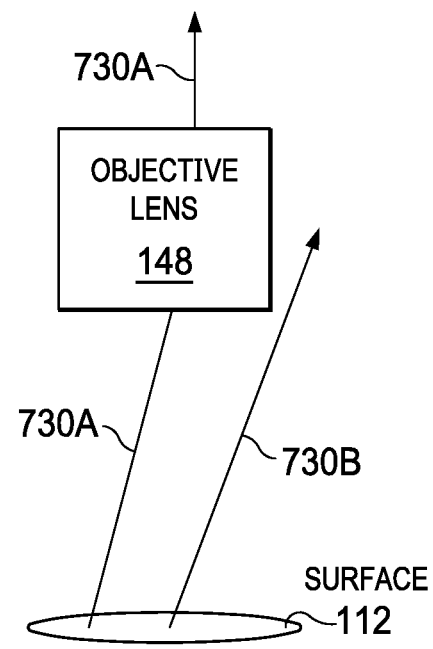
FIG. 7E illustrates a second example of an objective lens receiving portions of a laser beam reflected off a test surface.
Figure 7F:
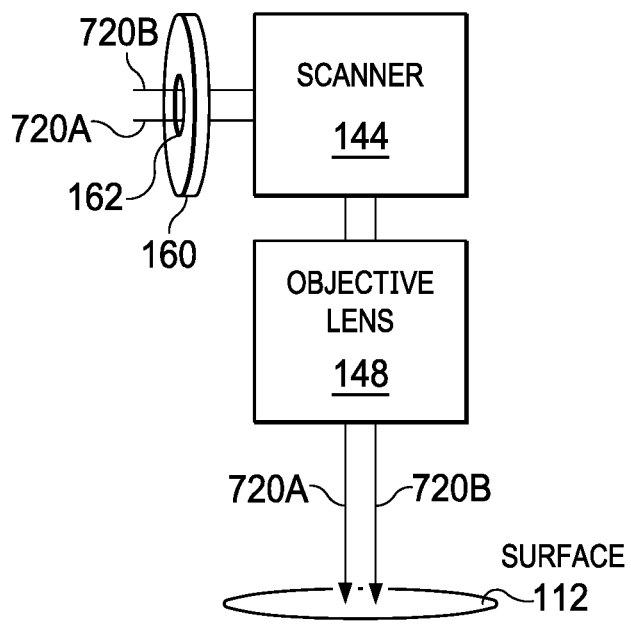
FIG. 7F illustrates an example of a diaphragm and an objective lens providing portions of a laser beam to a test surface.
Figure 7G:
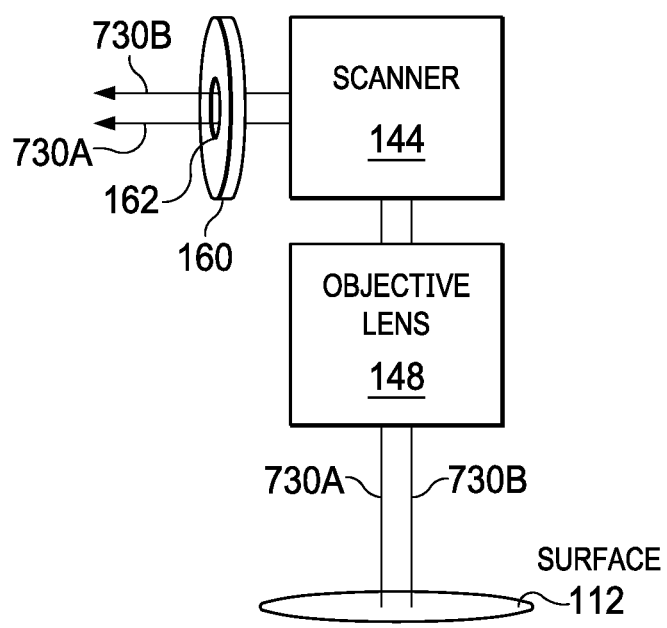
FIG. 7G illustrates an example of a diaphragm and an objective lens receiving portions of a laser beam reflected off a test surface.
Figure 7H:
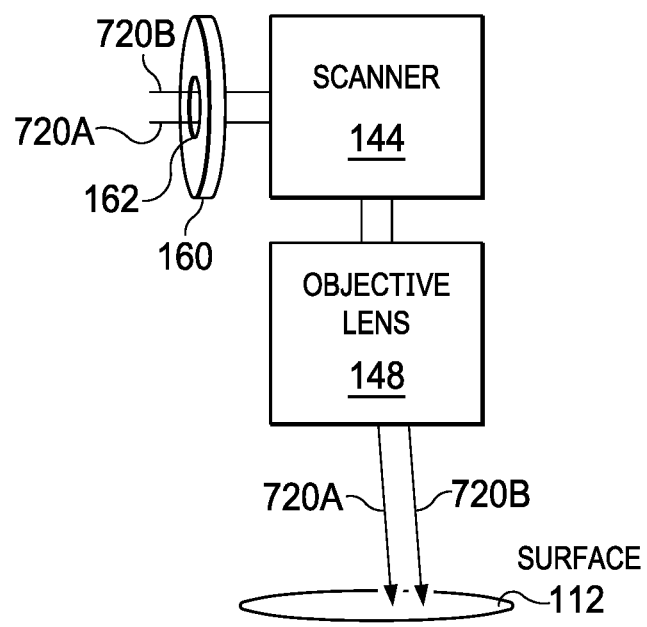
FIG. 7H illustrates another example of a diaphragm and an objective lens providing portions of a laser beam to a test surface.

At 615, the multiple first portions of the laser beam may be provided to respective multiple locations of a test surface. In one example, objective lens 148 may provide the multiple first portions of the laser beam to respective multiple locations 710A-710M of surface 112, as illustrated in FIG. 7A. In a second example, objective lens 148 may provide multiple first portions 720A-720C of the laser beam to respective multiple locations of surface 112, as illustrated in FIG. 7B. In a third example, objective lens 148 may provide multiple first portions 720A and 720B of the laser beam to respective multiple locations of surface 112, as illustrated in FIG. 7D. In a fourth example, objective lens 148 may provide multiple first portions 720A and 720B of the laser beam to respective multiple locations of surface 112, as illustrated in FIG. 7F. In another example, objective lens 148 may provide multiple first portions 720A and 720B of the laser beam to respective multiple locations of surface 112, as illustrated in FIG. 7H. First portions 720 of the laser beam may include multiple photons. Although surface 112 is illustrated as circular in FIGS. 7A-7M, surface 112 may be any shape. For example, surface 112 may be rectangular, polygonal, etc. Providing the multiple first portions of the laser beam to respective multiple locations of a test surface may include utilizing scanner 144. For example, the multiple first portions of the laser beam may be controlled via scanner 144 to sequentially provide to respective multiple locations of the test surface.

Figure 7I:
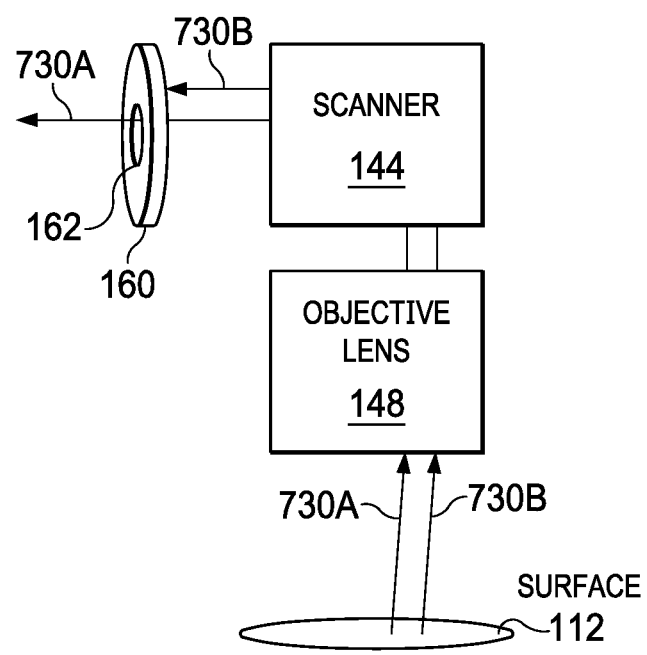
FIG. 7I illustrates an example of an objective lens receiving portions of a laser beam reflected off a test surface and a diaphragm blocking portions of the laser beam.

At 620, multiple second portions of the laser beam may be received from the test surface. For example, objective lens 148 may receive multiple second portions of the laser beam from surface 112. The second portions of the laser beam may be reflected by the test surface. In one example, second portions 730A-730C of the laser beam may be reflected by surface 112, as illustrated in FIG. 7C. In a second example, second portions 730A and 730B of the laser beam may be reflected by surface 112, as shown in FIG. 7E. In a third example, second portions 730A and 730B of the laser beam may be reflected by surface 112, as illustrated in FIG. 7G. In another example, second portions 730A and 730B of the laser beam may be reflected by surface 112, as shown in FIG. 7I. Second portions 730 of the laser beam may include multiple photons. For example, second portions 730 of the laser beam may include multiple photons of the multiple photons associated with first portions 720 of the laser beam. As illustrated in FIG. 7E, objective lens 148 may not receive second portions 730B of the laser beam. For example, second portions 730B may not be reflected to objective lens 148, as shown in FIG. 7E. As illustrated in FIG. 7I, diaphragm 160 may block or obstruct second portions 730B. For example, diaphragm 160 may block or obstruct second portions 730B from reaching TPA detector 130. The second portions of the laser beam may be respectively associated with the multiple first portions of the laser beam reflected from the test surface.

At 625, the multiple second portions of the laser beam may be provided to a TPA detector. For example, the multiple second portions of the laser beam may be provided to TPA detector 130. One or more of multiple second portions 730A-730C may be provided to TPA detector 130. Providing the multiple second portions of the laser beam to the TPA detector may include directing the multiple second portions of the laser beam to the TPA detector. For example, one or more of scanner 144, beam expander 141, waveplate 134, polarizer 124, and lens 128 may direct one or more of multiple second portions 730A-730C of the laser beam to TPA detector 130.

At 630, multiple intensities respectively associated with the multiple second portions of the laser beam may be determined. For example, TPA detector 130 may determine multiple intensities respectively associated with the multiple second portions of the laser beam. Second portions 730A-730C may be associated with respective multiple intensities. Second portions 730A-730C may be associated with respective same or similar multiple intensities. In one example, TPA detector 130 may determine a first intensity associated with multiple second portions 730A of the laser beam. In a second example, TPA detector 130 may determine a second intensity associated with multiple second portions 730A and 730B of the laser beam. The second intensity may be greater than the first intensity. In another example, TPA detector 130 may determine a third intensity associated with multiple second portions 730A-730C of the laser beam. The third intensity may be greater than the second intensity. Although three multiple second portions 730A-730C are illustrated as examples, other multiple second portions 730 may be present and/or utilized.

At 635, the multiple intensities may be transformed into data that represents multiple measurements of the multiple intensities. In one example, TPA detector 130 may transform the multiple intensities into data that represents multiple measurements of the multiple intensities. TPA detector 130 may provide the data that represents multiple measurements of the multiple intensities to computer system 152. TPA detector 130 may transform the first intensity associated with multiple second portions 730A of the laser beam into first data that represents a measurement value of the first intensity. TPA detector 130 may transform the second intensity associated with multiple second portions 730A and 730B of the laser beam into second data that represents a measurement value of the second intensity. TPA detector 130 may transform the third intensity associated with multiple second portions 730A-730C of the laser beam into third data that represents a measurement value of the third intensity.

In another example, an analog to digital converter (ADC) may transform signals from TPA detector 130 associated with the multiple intensities into digital data that represents multiple measurements of the multiple intensities. The ADC may transform analog signals from TPA detector 130 associated with the first intensity associated with multiple second portions 730A of the laser beam into first data that represents a measurement value of the first intensity. The ADC may transform analog signals from TPA detector 130 associated with the second intensity associated with multiple second portions 730A and 730B of the laser beam into second data that represents a measurement value of the second intensity. The ADC may transform analog signals from TPA detector 130 associated with the third intensity associated with multiple second portions 730A-730C of the laser beam into third data that represents a measurement value of the third intensity.

Computer system 152 may receive the data that represents multiple measurements of the multiple intensities. In one example, computer system 152 may receive the first data that represents the measurement value of the first intensity. In a second example, computer system 152 may receive the second data that represents the measurement value of the second intensity. In another example, computer system 152 may receive the third data that represents the measurement value of the third intensity.

At 640, it may be determined, from the data, if an intensity value of the multiple intensities is below a threshold intensity value. The intensity value of the multiple intensities may be a peak intensity value as photons of a portion of the laser beam may behave as a wave. The threshold intensity value may be a minimum intensity value. An intensity value may be below the threshold intensity value if portions of the laser beam are not received by objective lens 148. In one example, portions 730B of the laser beam may not be received by objective lens 148, as illustrated in FIG. 7E. In another example, diaphragm 160 may block portions 730B of the laser beam, as illustrated in FIG. 7I. Any of these examples may contribute to the intensity value being below the threshold intensity value or may cause the intensity value being below the threshold intensity value. If portions of the laser beam are not received by objective lens 148, the portions of the laser beam may not be provided to TPA detector 130.

Figure 7J:
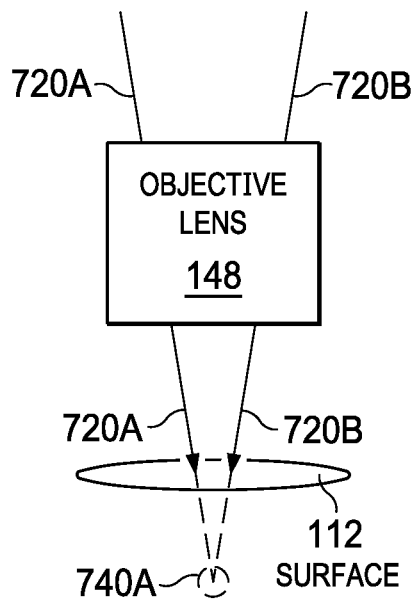
FIG. 7J illustrates an example of one or more aberrations of an objective lens causing a focus of the objective lens to be beyond a test surface.
Figure 7K:
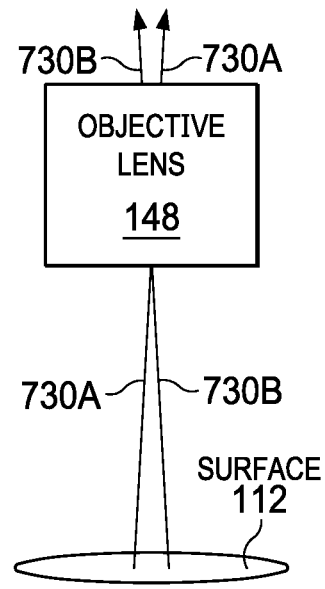
FIG. 7K illustrates an example of reflected portions of a laser beam not returning along incident paths of the laser beam.
Figure 7L:
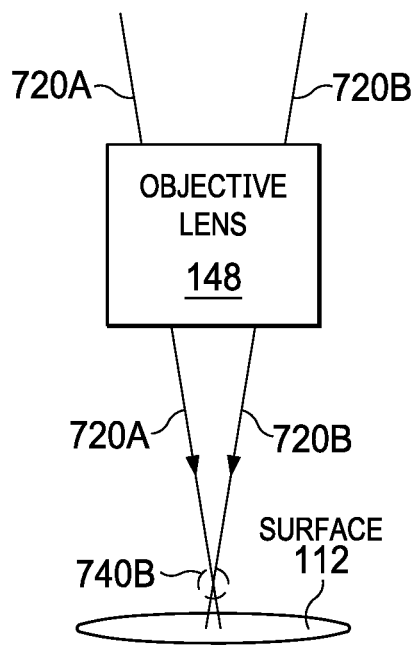
FIG. 7L illustrates an example of one or more aberrations of an objective lens causing a focus of the objective lens to be short of a test surface.
Figure 7M:
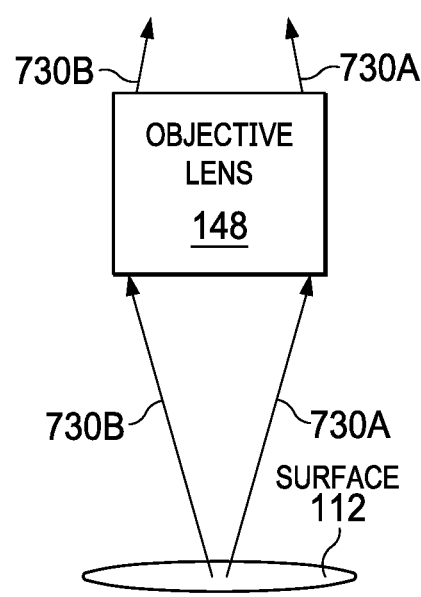
FIG. 7M illustrates another example of reflected portions of a laser beam not returning along incident paths of the laser beam.

One or more aberrations of objective lens 148 may cause one or more errors in one or more focuses of objective lens 148. In one example, the one or more aberrations of objective lens 148 may cause a focus of objective lens 148 to be beyond surface 112, as illustrated in FIG. 7K. As shown, a focus point 740A may be beyond surface 112. As illustrated in FIG. 7L, second portions 730A and 730B may not return along paths associated with first portions 720A and 720B, respectively. In another example, the one or more aberrations of objective lens 148 may cause a focus of objective lens 148 to be short of surface 112, as shown in FIG. 7M. As shown, a focus point 740B may be short of surface 112. As illustrated in FIG. 7N, second portions 730A and 730B may not return along paths associated with first portions 720A and 720B, respectively.

When objective lens 148 causes first portions 720 to not be focused on surface 112 at a location 710, second portions 730 may not return along paths associated with first portions 720. For example, objective lens 148 may cause a focus 740 of first portions 720 to not be on surface 120, as illustrated in FIGS. 7J and 7L. When second portions 730 do not return along paths associated with first portions 720, one or more intensities of the second portions of the laser beam may be diminished. In one example, second portions 730 may not return along paths associated with first portions 720, as shown in FIGS. 7K, and 7M. In another example, second portions 730, as illustrated in FIGS. 7E and 7I, may be caused by objective lens 148 not focusing first portions 720 on surface 112, as shown in FIGS. 7D and 7H, respectively.

If the intensity value of the multiple intensities is below the threshold intensity value, information that indicates an issue associated with the objective lens may be provided, at 645. Providing the information that indicates the issue associated with the objective lens may include one or more of displaying, via a display, the information that indicates the issue associated with the objective lens; storing, via a memory medium, the information that indicates the issue associated with the objective lens; and sending, to a network, the information that indicates the issue associated with the objective lens, among others. If the information that indicates an issue associated with an objective lens, the objective lens may be repaired or replaced.

If the intensity value of the multiple intensities is not below the threshold intensity value, information that indicates there is no issue associated with the objective lens may be provided, at 650. Providing the information that indicates there is no issue associated with the objective lens may include one or more of displaying, via a display, the information that indicates there is no issue associated with the objective lens; storing, via a memory medium, the information that indicates there is no issue associated with the objective lens; and sending, to a network, the information that indicates there is no issue associated with the objective lens, among others.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A medical system, comprising:
   at least one processor;
   a two-photon absorption (TPA) detector coupled to the at least one processor; and
   a non-transitory memory medium that is coupled to the at least one processor and that includes instructions executable by the at least one processor;
   wherein the instruction, when executed by the at least one processor, cause the system to:
      provide a plurality of first portions of a laser beam to an objective lens of an optical system;
      provide, via the objective lens, the plurality of first portions of the laser beam along a plurality of first paths to a respective plurality of locations of a test surface;
      receive, via the objective lens, a plurality of second portions of the laser beam along a plurality of second paths from the test surface, a second portion associated with a first portion reflected from the test surface; and
      provide the plurality of second portions of the laser beam to the TPA detector;
   wherein the TPA detector is configured to:
      determine a plurality of intensities respectively associated with the plurality of second portions of the laser beam; and
      transform the plurality of intensities into data that represents a plurality of intensity values of the plurality of intensities; and
   wherein the instructions further cause the system to:
      determine, from the data, if an intensity value of the plurality of intensities is below a threshold intensity value;
      when the intensity value of the plurality of intensities is below the threshold intensity value:
         determine that the second path of the second portion associated with the intensity value is different from the first path of the associated first portion in that the second path bypasses the objective lens;
         establish that an issue associated with the objective lens is that the second path bypasses the objective lens; and
         provide information that indicates the second path bypasses the objective lens; and
      when the intensity value of the plurality of intensities is not below the threshold intensity value, provide information that indicates there is no issue associated with the objective lens.

2. The system of claim 1, further comprising:
   a laser configured to generate the laser beam.

3. The system of claim 1, further comprising:
   a biometry device that includes the optical system.

4. The system of claim 1, wherein the objective lens includes a F-theta lens.

5. The system of claim 1,
   wherein the optical system includes at least one mirror; and
   wherein the instructions further cause the system to:
   adjust the at least one mirror to provide the plurality of first portions of the laser beam to the respective plurality of locations of the test surface.

6. The system of claim 1, further comprising:
   a plurality of lenses, different from the objective lens;
   wherein the instructions further cause the system to adjust the plurality of lenses to expand respective diameters of the plurality of first portions of the laser beam.

7. The system of claim 1,
   wherein the instructions further cause the system to adjust a diameter of an aperture of a diaphragm; and
   wherein the diaphragm permits light, reflected from the test surface, to pass through the aperture and blocks the light, reflected from the test surface, outside the aperture.

8. The system of claim 7, wherein the optical system includes the diaphragm.

9. The system of claim 1, wherein the issue associated with the objective lens is an optical aberration.

10. The system of claim 1, wherein the test surface is partially reflective.

11. The system of claim 1, wherein the instructions further cause the system to establish that there is an issue associated with the objective lens in response to the determination by:
    determining that the objective lens fails to focus the associated first portion on the test surface.

12. The system of claim 1, wherein the instructions further cause the system to establish that there is an issue associated with the objective lens in response to the determination by:
    determining that the objective lens fails to focus the associated first portion on the respective location of the test surface.

13. A method of testing an objective lens of an optical system, comprising:
    providing a plurality of first portions of a laser beam to the objective lens of the optical system;
    the objective lens providing the plurality of first portions of the laser beam along a plurality of first paths to a respective plurality of locations of a test surface;
    the objective lens receiving a plurality of second portions of the laser beam along a plurality of second paths from the test surface, a second portion associated with a first portion reflected from the test surface;
    providing the plurality of second portions of the laser beam to a two-photon absorption (TPA) detector;
    the TPA detector determining a plurality of intensities respectively associated with the plurality of second portions of the laser beam;
    the TPA detector transforming the plurality of intensities into data that represents a plurality of intensity values of the plurality of intensities;
    determining, from the data, if an intensity value of the plurality of intensities is below a threshold intensity value;
    when the intensity value of the plurality of intensities is below the threshold intensity value:
       determining that the second path of the second portion associated with the intensity value is different from the first path of the associated first portion in that the second path bypasses the objective lens;
       establishing that an issue associated with the objective lens is that the second path bypasses the objective lens; and
       providing information that indicates the second path bypasses the objective lens; and
    when the intensity value of the plurality of intensities is not below the threshold intensity value, providing information that indicates there is no issue associated with the objective lens.

14. The method of claim 13, wherein a medical system includes the optical system.

15. The method of claim 14, wherein the medical system includes a biometry device that includes the optical system.

16. The method of claim 13, wherein the objective lens includes a F-theta lens.

17. The method of claim 13, wherein the optical system includes at least one mirror;
  the method further comprising:
  adjusting the at least one mirror to provide the plurality of first portions of the laser beam to the respective plurality of locations of the test surface.

18. The method of claim 13, wherein the optical system includes a plurality of lenses, different from the objective lens;
  the method further comprising:
  adjusting the plurality of lenses to expand respective diameters of the plurality of first portions of the laser beam.

19. The method of claim 13, further comprising:
  adjusting a diameter of an aperture of a diaphragm;
  wherein the diaphragm permits light, reflected from the test surface, to pass through the aperture and blocks the light, reflected from the test surface, outside the aperture.

20. The method of claim 19, wherein the optical system includes the diaphragm.

21. The method of claim 13, wherein the issue associated with the objective lens is an optical aberration.

22. The method of claim 13, wherein the test surface is partially reflective.

23. The method of claim 13, wherein establishing that there is an issue associated with the objective lens in response to the determination comprises:
  determining that the objective lens fails to focus the associated first portion on the test surface.

24. The method of claim 13, wherein establishing that there is an issue associated with the objective lens in response to the determination comprises:
  determining that the objective lens fails to focus the associated first portion on the respective location of the test surface.

\* \* \* \* \*